(12) United States Patent
Mormile et al.

(10) Patent No.: US 11,937,603 B2
(45) Date of Patent: Mar. 26, 2024

(54) MALEIMIDE DERIVATIVES HAVING HERBICIDAL ACTIVITY, AGRONOMIC COMPOSITIONS OF THE MALEIMIDE DERIVATIVES, AND USES THEREOF

(71) Applicant: Gowan Company, LLC, Yuma, AZ (US)

(72) Inventors: Silvia Mormile, Novara (IT); Marilena Gusmeroli, Monza (IT); Paolo Boggio, Turin (IT); Paolo Bellandi, Carcare (IT); Ivan Bondoni, Santo Stefano Ticino (IT); Gabriele Piazzon, Cameri (IT); Riccardo Liguori, Monza (IT)

(73) Assignee: GOWAN COMPANY, LLC, Yuma, AZ (US)

( * ) Notice: Subject to any disclaimer, the term of this patent is extended or adjusted under 35 U.S.C. 154(b) by 757 days.

(21) Appl. No.: 16/968,555

(22) PCT Filed: Feb. 7, 2019

(86) PCT No.: PCT/IB2019/050995
§ 371 (c)(1),
(2) Date: Aug. 7, 2020

(87) PCT Pub. No.: WO2019/155400
PCT Pub. Date: Aug. 15, 2019

(65) Prior Publication Data
US 2020/0375186 A1 Dec. 3, 2020

(30) Foreign Application Priority Data
Feb. 8, 2018 (IT) .................. 102018000002503

(51) Int. Cl.
*A01N 43/80* (2006.01)
*C07D 413/04* (2006.01)
*C07F 7/08* (2006.01)

(52) U.S. Cl.
CPC ........... *A01N 43/80* (2013.01); *C07D 413/04* (2013.01); *C07F 7/0814* (2013.01)

(58) Field of Classification Search
None
See application file for complete search history.

(56) References Cited

U.S. PATENT DOCUMENTS 4,138,243 A * 2/1979 Bohner .................. A01N 43/40
544/212
4,828,604 A 5/1989 Kume et al.
(Continued)

FOREIGN PATENT DOCUMENTS

CH 633678 A5 12/1982
EP 0286816 A1 10/1988
(Continued)

OTHER PUBLICATIONS

International Search Report and Written Opinion in corresponding International Application No. PCT/IB2019/050995 dated Jun. 18, 2019, 17 pages.

Primary Examiner — Erin E Hirt
(74) Attorney, Agent, or Firm — Florek & Endres PLLC

(57) ABSTRACT

Compounds of general formula (I), isomers, salts, or hydrates thereof.

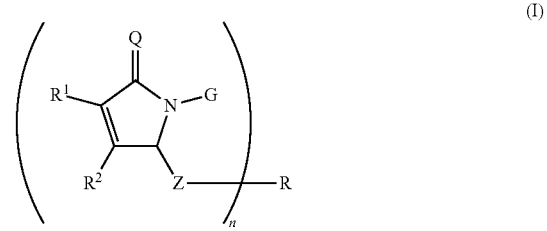

(I)

Herbicide compositions including: at least one compound of general formula (I); at least one solvent and/or at least one diluent; and, optionally, at least one agronomically acceptable excipient.

Processes for preparing the compounds of general formula (I), the processes including: reacting a compound of general formula (II) with at least one compound of general formula (III) in a presence of at least one base, according to:

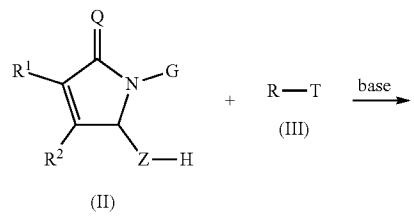

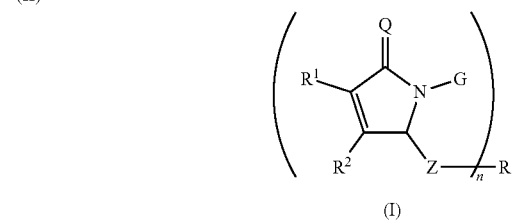

(I)

Processes for preparing the compounds of general formula (I), the processes including: reacting a compound of general formula (VI) with at least one compound of general formula (VII) in a presence of at least one base, according to:

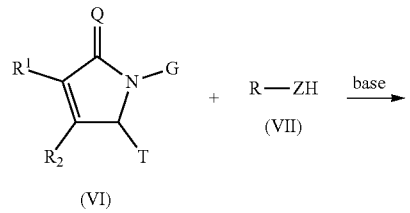

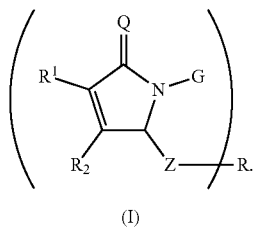

(I)

20 Claims, No Drawings

(56) References Cited

U.S. PATENT DOCUMENTS

| | | |
|---|---|---|
| 4,845,230 A | 7/1989 | Kume et al. |
| 4,909,828 A | 3/1990 | Kume et al. |
| 5,045,108 A | 9/1991 | Elbe et al. |

FOREIGN PATENT DOCUMENTS

| | | |
|---|---|---|
| EP | 0297378 A2 | 1/1989 |
| EP | 0339390 A1 | 11/1989 |
| EP | 0403891 A1 | 12/1990 |
| WO | 2014180740 A1 | 11/2014 |
| WO | 2015018433 A1 | 2/2015 |
| WO | 2015018434 A1 | 2/2015 |
| WO | 2016071359 A1 | 5/2016 |
| WO | 2016071360 A1 | 5/2016 |
| WO | 2018114663 A1 | 6/2018 |

* cited by examiner

MALEIMIDE DERIVATIVES HAVING HERBICIDAL ACTIVITY, AGRONOMIC COMPOSITIONS OF THE MALEIMIDE DERIVATIVES, AND USES THEREOF

CROSS-REFERENCE TO RELATED APPLICATION(S)

This application is a national stage entry from International Application No. PCT/IB2019/050995, filed on Feb. 7, 2019, in the Receiving Office ("RO/LB") of the International Bureau of the World Intellectual Property Organization ("WIPO"), published as International Publication No. WO 2019/155400 A1 on Aug. 15, 2019; International Application No. PCT/IB2019/050995 claims priority under 35 U.S.C. § 119 from Italian Patent Application No. 102018000002503, filed on Feb. 8, 2018, in the Italian Patent and Trademark Office ("IPTO"), the entire contents of all of which are incorporated herein by reference.

The present invention relates to new maleimides having general formula (I), their isomers, salts and hydrates:

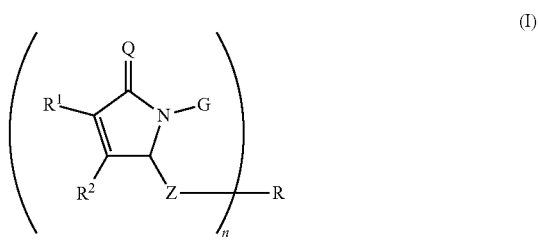

and their use as herbicides.

DESCRIPTION

The present invention relates to new substituted maleimides.

More specifically, the present invention relates to new substituted maleimides having a high herbicidal activity and their use as herbicides for the control of weeds in agricultural crops.

Patent applications EP297378, U.S. Pat. No. 4,845,230 and more recently WO2016/071360 describe hydroxymaleimides having general formula:

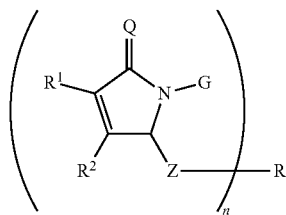

for use as herbicides.

Furthermore, maleimides have been described in which the hydroxyl radical is appropriately acylated, as for example in patent applications EP286816, EP339390 or W2014/180740.

The doses of use indicated in the above-mentioned patent applications, however, are extremely high and are therefore likely to create problems relating to environmental impact in addition to phytotoxicity for the crops treated.

The Applicant has now surprisingly found that, by suitably modifying the substituents present on the maleimide ring, products are obtained, provided with a considerable herbicidal activity against numerous weeds with significantly reduced doses of use. At the same time, these products exhibit low or no phytotoxicity for crops of agricultural interest and can therefore also be used as selective herbicides.

An object of the present invention therefore relates to new maleimides having general formula (I)

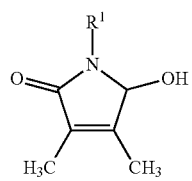

wherein

R represents a $C_3$-$C_{18}$ cycloalkylcarbonyl group, a $C_3$-$C_{18}$ cycloalkylthiocarbonyl group, a $C_7$-$C_{12}$ alkylcarbonyl group, a $C_3$-$C_{18}$ cycloalkoxycarbonyl group, a $C_3$-$C_{18}$cycloalkyl$C_1$-$C_6$ alkylcarbonyl group, a $C_3$-$C_{18}$cycloalkyl$C_1$-$C_{12}$alkylthiocarbonyl group, a $C_1$-$C_{12}$alkoxy$C_1$-$C_{12}$alkylcarbonyl group, a $C_1$-$C_{12}$alkoxy$C_1$-$C_{12}$alkylthiocarbonyl group, a $C_3$-$C_{18}$cycloalkoxy$C_1$-$C_{12}$alkylcarbonyl group, a $C_3$-$C_{18}$cycloalkoxy$C_1$-$C_{12}$alkylthiocarbonyl group, a $C_1$-$C_{12}$alkylthio$C_1$-$C_{12}$alkylcarbonyl group, a $C_3$-$C_{18}$cycloalkylthio$C_1$-$C_{12}$alkylcarbonyl group, a $C_1$-$C_{12}$ alkylcarboxy$C_1$-$C_{12}$alkylcarbonyl group, a $C_3$-$C_1$ cycloalkylcarboxy$C_1$-$C_{12}$alkylcarbonyl group, a $C_1$-$C_{12}$alkylcarbonyl$C_1$-$C_{12}$alkylcarbonyl group, a $C_3$-$C_1$ cycloalkylcarbonyl$C_1$-$C_{12}$alkylcarbonyl group, a $C_1$-$C_{12}$alkoxy$C_1$-$C_{12}$alkoxycarbonyl group, a $C_3$-$C_1$cycloalkoxy$C_1$-$C_{12}$ alkoxycarbonyl group, a $C_1$-$C_{12}$alkylthio$C_1$-$C_{12}$alkoxycarbonyl group, a $C_3$-$C_{18}$cycloalkylthio$C_1$-$C_{12}$alkoxycarbonyl group, a $C_3$-$C_1$ cycloalkylcarboxy$C_1$-$C_{12}$alkoxycarbonyl group, an aryl$C_1$-$C_{12}$ alkoxycarbonyl group, a $C_1$-$C_{12}$alkoxy$C_2$-$C_{12}$alkyl group, an aryloxy$C_1$-$C_{12}$alkyl group, a benzyloxy$C_2$-$C_{12}$alkyl group, a $C_3$-$C_{18}$cycloalkoxy$C_1$-$C_{12}$alkyl group, a $C_1$-$C_{12}$alkylcarboxy$C_1$-$C_{12}$alkyl group, a $C_3$-Clecycloalkylcarboxy$C_1$-$C_{12}$alkyl group, a $C_1$-$C_{12}$alkylthio$C_1$-$C_{12}$alkyl group, a $C_3$-$C_{18}$cycloalkylthio$C_1$-$C_{12}$alkyl group, a $C_1$-$C_{12}$alkylcarbonyl$C_1$-$C_{12}$alkyl group, a $C_3$-$C_{18}$cycloalkylcarbonyl$C_1$-$C_{12}$alkyl group, a $C_1$-$C_{12}$alkoxycarbonyl$C_1$-$C_{12}$alkyl group, a $C_3$-$C_{18}$cycloalkoxycarbonyl$C_1$-$C_{12}$alkyl group, a $C_2$-$C_6$ haloalkenylcarbonyl group, a $R^3R^4R^5Si$ group, a CO—COOR$^3$ group, a COCR$^3{}_2$COOR$^3$ group, a bifunctional —SiR$^3$R$^4$ $(CH_2)_m$SiR$^3$R$^4$— group, a bifunctional —(CO—CO)— group, a bifunctional —(COCR$^3{}_2$CO)— group, a bifunctional —[COO$(CH_2)_m$OCO]— group;

R$^1$ and R$^2$, the same as or different from each other, represent a halogen atom, a $C_1$-$C_{12}$ alkyl, a $C_1$-$C_{12}$ haloalkyl, a $C_3$-$C_{18}$ cycloalkyl, a $C_1$-$C_{12}$ alkoxyl, a $C_3$-$C_{18}$ cycloalkoxyl;

Z represents an O atom, an S atom or a NR$^4$ group;

Q represents an O atom, an S atom, a NOR$^3$ group, a NR$^3$R$^4$ group, a C=CR$^3$R$^4$ group;

$R^3$, $R^4$, $R^5$, the same as or different from each other, represent a hydrogen atom, a $C_1$-$C_{12}$ alkyl, a $C_1$-$C_{12}$ haloalkyl, a $C_3$-$C_{18}$ cycloalkyl;

m is an integer from 1 to 5;

n is 1 or 2;

G represents an aromatic heterocyclic ring with 5 or 6 terms selected from:

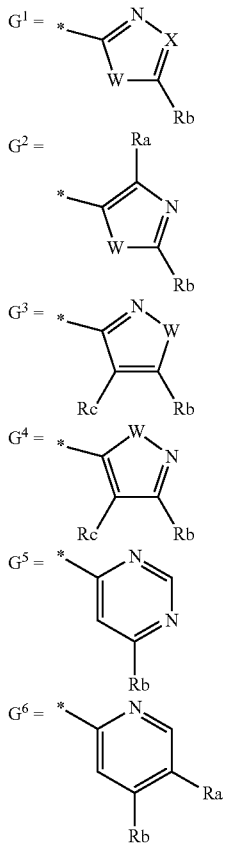

and wherein:

X represents a nitrogen atom or a CRa group;

W represents an oxygen atom, or a sulphur atom or a NRa group;

Ra, Rb, Rc, the same as or different from each other, represent a hydrogen atom, a halogen atom, a $C_1$-$C_{12}$ alkyl, a $C_2$-$C_{12}$ alkenyl, a $C_2$-$C_{12}$ haloalkenyl, a $C_3$-$C_{18}$ cycloalkenyl, a $C_3$-$C_{18}$ cycloalkyl, a $C_2$-$C_{12}$ alkynyl, a $C_1$-$C_{12}$ haloalkyl, a $C_1$-$C_{12}$ alkoxyl, a $C_1$-$C_{12}$ haloalkoxyl, a $C_3$-$C_{18}$ cycloalkoxyl, a CN group, a $B(OR^3)_2$ group, a 4,4,5,5-tetramethyl-1,3,2-dioxaborolanyl group; with the proviso that when:

(i) R represents a cyclopropylcarbonyl group, a cyclohexylcarbonyl group or a 3-ketobutanoyl group, and (ii) $R^1$ and $R^2$ are both methyl, and (iii) Q and Z are oxygen atoms, and (iv) n is equal to 1, then G is different from $G^6$ in which Ra and Rb are both hydrogen or in which Ra is a methyl group and Rb is hydrogen.

Compounds of Formula (I) are preferred wherein:

R represents a $C_3$-$C_{12}$ cycloalkylcarbonyl group, a $C_3$-$C_{12}$ cycloalkylthiocarbonyl group, a $C_7$-$C_{12}$ alkylcarbonyl group, a $C_3$-$C_{12}$ cycloalkoxycarbonyl group, a $C_3$-$C_{12}$cycloalkyl$C_1$-$C_6$ alkylcarbonyl group, a $C_3$-$C_{12}$cycloalkyl$C_1$-$C_6$alkylthiocarbonyl group, a $C_1$-$C_6$alkoxy$C_1$-$C_6$alkylcarbonyl group, a $C_1$-$C_6$alkoxy$C_1$-$C_6$alkylthiocarbonyl group, a $C_3$-$C_{12}$cycloalkoxy$C_1$-$C_6$alkylcarbonyl group, a $C_3$-$C_{12}$cycloalkoxy$C_1$-$C_6$alkylthiocarbonyl group, a $C_1$-$C_6$alkylthio$C_1$-$C_6$alkylcarbonyl group, a $C_3$-$C_{12}$cycloalkylthio$C_1$-$C_6$alkylcarbonyl group, a $C_1$-$C_6$ alkylcarboxy$C_1$-$C_6$alkylcarbonyl group, a $C_3$-$C_{12}$ cycloalkylcarboxy$C_1$-$C_6$alkylcarbonyl group, a $C_1$-$C_6$alkylcarbonyl$C_1$-$C_6$alkylcarbonyl group, a $C_3$-$C_{12}$ cycloalkylcarbonyl$C_1$-$C_6$alkylcarbonyl group, a $C_1$-$C_6$alkoxy$C_1$-$C_6$alkoxycarbonyl group, a $C_3$-$C_{12}$cycloalkoxy$C_1$-$C_6$ alkoxycarbonyl group, a $C_1$-$C_6$alkylthio$C_1$-$C_6$alkoxycarbonyl group, a $C_3$-$C_{12}$cycloalkylthio$C_1$-$C_6$alkoxycarbonyl group, a $C_3$-$C_{12}$ cycloalkylcarboxy$C_1$-$C_6$alkoxycarbonyl group, an aryl$C_1$-$C_6$ alkoxycarbonyl group, a $C_1$-$C_6$alkoxy$C_2$-$C_7$alkyl group, an aryloxy$C_1$-$C_6$alkyl group, a benzyloxy$C_2$-$C_7$alkyl group, a $C_3$-$C_{12}$cycloalkoxy$C_1$-$C_6$alkyl group, a $C_1$-$C_6$alkylcarboxy$C_1$-$C_6$alkyl group, a $C_3$-$C_{12}$cycloalkylcarboxy$C_1$-$C_6$alkyl group, a $C_1$-$C_6$alkylthio$C_1$-$C_6$alkyl group, a $C_3$-$C_{12}$cycloalkylthio$C_1$-$C_6$alkyl group, a $C_1$-$C_6$alkylcarbonyl$C_1$-$C_6$alkyl group, a $C_3$-$C_{12}$cycloalkylcarbonyl$C_1$-$C_6$alkyl group, a $C_1$-$C_{12}$alkoxycarbonyl$C_1$-$C_{12}$alkyl group, a $C_3$-$C_{12}$cycloalkoxycarbonyl$C_1$-$C_{12}$alkyl group, a $C_2$-$C_6$ haloalkenylcarbonyl group, a $R^3R^4R^5$Si group, a CO—COOR$^3$ group, a COCR$^3_2$COOR$^3$ group, a bifunctional —SiR$^3R^4$ (CH$_2$)$_m$SiR$^3R^4$— group, a bifunctional —(CO—CO)— group, a bifunctional —(COCR$^3_2$CO)— group, a bifunctional —[COO(CH$_2$)$_m$OCO]— group;

$R^1$ and $R^2$, the same as or different from each other, represent a halogen atom, a $C_1$-$C_6$ alkyl, a $C_1$-$C_6$ haloalkyl, a $C_3$-$C_{12}$ cycloalkyl, a $C_1$-$C_6$ alkoxyl, a $C_3$-$C_{12}$ cycloalkoxyl;

Z represents an O atom, an S atom or a NR$^4$ group;

Q represents an O atom, an S atom, a NOR$^3$ group, a NR$^3$R$^4$ group, a C=CR$^3$R$^4$ group;

$R^3$, $R^4$, $R^5$, the same as or different from each other, represent a hydrogen atom, a $C_1$-$C_6$ alkyl, a $C_1$-$C_6$ haloalkyl, a $C_3$-$C_{12}$ cycloalkyl;

m is an integer from 1 to 5;

n is 1 or 2;

G represents an aromatic heterocyclic ring with 5 or 6 terms selected from:

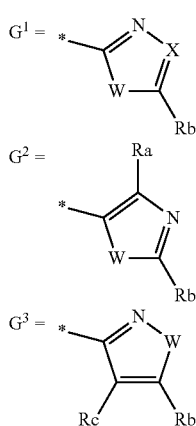

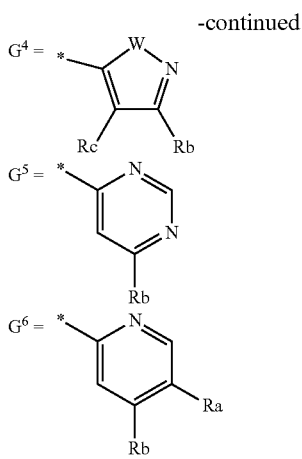

and wherein:
X represents a nitrogen atom or a CRa group;
W represents an oxygen atom, or a sulphur atom or a NRa group;
Ra, Rb, Rc, the same as or different from each other, represent a hydrogen atom, a halogen atom, a $C_1$-$C_6$ alkyl, a $C_2$-$C_7$ alkenyl, a $C_2$-$C_7$ haloalkenyl, a $C_3$-$C_{12}$ cycloalkenyl, a $C_3$-$C_2$ cycloalkyl, a $C_2$-$C_7$ alkynyl, a $C_1$-$C_6$ haloalkyl, a $C_1$-$C_6$ alkoxyl, a $C_1$-$C_6$ haloalkoxyl, a $C_3$-$C_{12}$ cycloalkoxyl, a CN group, a $B(OR^3)_2$ group, a 4,4,5,5-tetramethyl-1,3,2-dioxaborolanyl group;
with the proviso that when:
(i) R represents a cyclopropylcarbonyl group, a cyclohexylcarbonyl group or a 3-ketobutanoyl group, and
(ii) $R^1$ and $R^2$ are both methyl, and
(iii) Q and Z are oxygen atoms, and
(iv) n is equal to 1,
then G is different from $G^6$ in which Ra and Rb are both hydrogen or in which Ra is a methyl group and Rb is hydrogen.

$C_7$-$C_{12}$ alkylcarbonyl group refers to a radical having formula RxCO wherein Rx has the meaning of $C_7$-$C_{12}$ alkyl.

Examples of this group are heptancarbonyl, octancarbonyl, nonancarbonyl, decancarbonyl.

$C_1$-$C_{12}$alkoxy$C_1$-$C_{12}$alkylcarbonyl, $C_3$-$C_{18}$cycloalkoxy$C_1$-$C_{12}$ alkylcarbonyl groups refer to a radical having formula RxORyCO wherein Rx has the meanings of $C_1$-$C_{12}$ alkyl, and $C_3$-$C_{18}$ cycloalkyl respectively, and Ry the meaning of $C_1$-$C_{12}$ alkyl.

Examples of these groups are methoxymethylcarbonyl, isopropoxymethylcarbonyl, cyclopropoxymethylcarbonyl, methoxyethylcarbonyl, methoxypropylcarbonyl.

$C_1$-$C_{12}$alkylthio$C_1$-$C_{12}$alkylcarbonyl, $C_3$-$C_{18}$cycloalkylthio$C_1$-$C_{12}$ alkylcarbonyl groups refer to a radical having formula RxSRyCO wherein Rx has the meanings of $C_1$-$C_{12}$ alkyl, and $C_3$-$C_{18}$ cycloalkyl respectively, and Ry has the meaning of $C_1$-$C_{12}$ alkyl.

Examples of these groups are methylthiomethylcarbonyl, isopropylthiomethylcarbonyl, cyclopropylthiomethylcarbonyl.

$C_3$-$C_{18}$cycloalkyl$C_1$-$C_{12}$ alkylthiocarbonyl group refers to a radical having formula RxRyCS wherein Rx has the meanings of $C_3$-$C_{18}$ cycloalkyl respectively, and Ry has the meaning of $C_1$-$C_{12}$ alkyl.

Examples of these groups are cyclopropyl-methylthiocarbonyl, cyclohexylmethylthiocarbonyl.

$C_1$-$C_{12}$alkoxy$C_1$-$C_{12}$alkylthiocarbonyl, $C_3$-$C_{18}$cycloalkoxy$C_1$-$C_{12}$ alkylthiocarbonyl groups refer to a radical having formula RxORyCS wherein Rx has the meanings of $C_1$-$C_{12}$ alkyl and $C_3$-$C_{18}$ cycloalkyl, and Ry has the meaning of $C_1$-$C_{12}$ alkyl.

Examples of these groups are methoxymethylthiocarbonyl, isopropoxymethylthiocarbonyl, cyclopropoxymethylthiocarbonyl.

$C_1$-$C_{12}$alkylcarboxy$C_1$-$C_{12}$alkylcarbonyl and $C_3$-$C_{18}$cycloalkylcarboxy$C_1$-$C_{12}$alkylcarbonyl groups refer to a radical having formula RxOCORyCO wherein Rx has the meanings of $C_1$-$C_{12}$ alkyl, and $C_3$-$C_{18}$ cycloalkyl respectively, and Ry has the meaning of $C_1$-$C_{12}$ alkyl.

Examples of these groups are methylcarboxymethylcarbonyl, ethylcarboxymethylcarbonyl, cyclohexylcarboxymethylcarbonyl.

$C_1$-$C_{12}$alkylcarbonyl$C_1$-$C_{12}$alkylcarbonyl and $C_3$-$C_{18}$cycloalkylcarbonyl$C_1$-$C_{12}$alkylcarbonyl groups refer to a radical having formula RxCORyCO wherein Rx has the meanings of $C_1$-$C_{12}$ alkyl, and $C_3$-$C_{18}$ cycloalkyl respectively, and Ry has the meaning of $C_1$-$C_{12}$ alkyl.

Examples of these groups are acetylmethylcarbonyl, ethylcarbonylmethylcarbonyl, cyclopropylcarbonylmethyl carbonyl.

$C_1$-$C_{12}$alkoxy$C_1$-$C_{12}$alkoxycarbonyl and $C_3$-$C_{18}$cycloalkoxy$C_1$-$C_{12}$ alkoxycarbonyl groups refer to a radical having formula RxORyOCO wherein Rx has the meanings of $C_1$-$C_{12}$ alkyl, and $C_3$-$C_{18}$ cycloalkyl, respectively, and Ry has the meaning of $C_1$-$C_{12}$ alkyl.

Examples of these groups are methoxymethoxycarbonyl, ethoxymethoxycarbonyl, cyclopropoxymethoxycarbonyl.

$C_1$-$C_{12}$alkylthio$C_1$-$C_{12}$alkoxycarbonyl and $C_3$-$C_{18}$cycloalkylthio$C_1$-$C_{12}$ alkoxycarbonyl groups refer to a radical having formula RxSRyOCO wherein Rx has the meanings of $C_1$-$C_{12}$ alkyl, and $C_3$-$C_{18}$ cycloalkyl respectively, and Ry has the meaning of $C_1$-$C_{12}$ alkyl.

Examples of these groups are methylthiomethoxycarbonyl, ethylthiomethoxycarbonyl, cyclopropylthiomethoxycarbonyl.

$C_1$-$C_{12}$alkylcarboxy$C_1$-$C_{12}$alkoxycarbonyl and $C_3$-$C_{18}$cyclo-alkylcarboxy$C_1$-$C_{12}$alkoxycarbonyl groups refer to a radical having formula RxOCORyOCO wherein Rx has the meanings of $C_1$-$C_{12}$ alkyl, and $C_3$-$C_{18}$ cycloalkyl respectively, and Ry has the meaning of $C_1$-$C_{12}$ alkyl.

Examples of these groups are methylcarboxymethoxycarbonyl, ethylcarboxymethoxycarbonyl, cyclopropylcarboxymethoxycarbonyl.

Aryl$C_1$-$C_{12}$alkoxycarbonyl group refers to a radical having formula ArRxOCO wherein Rx has the meaning of $C_1$-$C_{12}$ alkyl respectively, and Ar has the meaning of mono, bi or tricyclic aromatic system, composed of carbon atoms only.

Examples of these groups are benzyloxycarbonyl, 2-phenyloxycarbonyl.

$C_1$-$C_{12}$ alkoxy$C_2$-$C_{12}$alkyl, aryloxy $C_1$-$C_{12}$ alkyl, benzyloxy $C_2$-$C_{12}$ alkyl, $C_3$-$C_{18}$cycloalkoxy$C_1$-$C_{12}$ alkyl groups refer to a radical having formula RxORy wherein Rx has the meanings of $C_1$-$C_{12}$ alkyl, aryl, benzyl and cycloalkyl $C_3$-$C_{18}$ respectively, and Ry has the meaning of $C_1$-$C_{12}$ alkyl.

Examples of these groups are ethoxymethyl, 2-phenoxyethyl, benzyloxymethyl, cyclopropoxymethyl.

$C_1$-$C_{12}$alkylcarboxy$C_1$-$C_{12}$alkyl, and $C_3$-$C_{18}$cycloalkylcarboxy$C_1$-$C_{12}$alkyl groups refer to a radical having the formula RxOCORy wherein Rx has the meanings of $C_1$-$C_{12}$ alkyl, and $C_3$-$C_{18}$ cycloalkyl respectively, and Ry has the meaning of $C_1$-$C_{12}$ alkyl.

Examples of these groups are methylcarboxymethyl, cyclopropylcarboxymethyl.

$C_1$-$C_{12}$alkylthio$C_1$-$C_{12}$ alkyl and $C_3$-$C_1$ cycloalkylthio$C_1$-$C_{12}$ alkyl groups refer to a radical having formula RxSRy wherein Rx has the meanings of $C_1$-$C_{12}$ alkyl, and $C_3$-$C_{18}$ cycloalkyl respectively, and Ry has the meaning of $C_1$-$C_{12}$ alkyl.

Examples of these groups are methylthiomethyl, cyclopropylthiomethyl.

$C_1$-$C_{12}$alkylcarbonyl$C_1$-$C_{12}$alkyl and $C_3$-Clcycloalkylcarbonyl$C_1$-$C_{12}$ alkyl groups refer to a radical having the formula RxCORy wherein Rx has the meanings of $C_1$-$C_{12}$ alkyl, and $C_3$-$C_{18}$ cycloalkyl respectively, and Ry has the meaning of $C_1$-$C_{12}$ alkyl.

Examples of these groups are acetylmethyl propanoylmethyl, cyclohexanoylmethyl.

$C_1$-$C_{12}$ alkoxycarbonyl$C_1$-$C_{12}$alkyl and $C_3$-$C_{18}$cycloalkoxycarbonyl $C_1$-$C_{12}$alkyl groups refer to a radical having formula RxOCORy wherein Rx has the meanings of $C_1$-$C_{12}$ alkyl, and $C_3$-$C_{18}$ cycloalkyl respectively, and Ry has the meaning of $C_1$-$C_{12}$ alkyl.

Examples of these groups are methoxycarbonylmethyl, isopropoxycarbonylmethyl, cyclpentoxycarbonylmethyl.

$C_2$-$C_6$haloalkenylcarbonyl refers to a radical having formula RxCO wherein Rx has the meaning of $C_2$-$C_6$ haloalkenyl.

Examples of this group are 3,3-difluoro-2-allylcarbonyl, 2,2-difluorovinylcarbonyl, 4,4-difluoro-3-butencarbonyl, 5,5-difluoro-4-pentencarbonyl, 6,6-difluoro-5-hexencarbonyl.

Examples of halogen are fluorine, chlorine, bromine, iodine.

Examples of $C_1$-$C_{12}$ alkyl are methyl, ethyl, n-propyl, isopropyl, n-butyl, isobutyl, sec-butyl, tert-butyl, n-pentyl, 3-methylbutyl, n-hexyl, 3,3-dimethylbutyl.

Examples of $C_1$-$C_{12}$ haloalkyl are fluoromethyl, difluoromethyl, trifluoromethyl, chloromethyl, dichloro-methyl, 2,2,2-trifluoroethyl, 1,1,2,2-tetrafluoroethyl, pentafluoroethyl, heptafluoropropyl, 4,4,4-trichloro-butyl, 4,4-difluoropentyl, 5,5-difluorohexyl.

Examples of $C_3$-$C_{18}$ cycloalkyl are cyclopropyl, cyclobutyl, cyclopentyl, cyclohexyl.

Examples of $C_2$-$C_{12}$ alkenyl are: ethenyl, propenyl, butenyl.

Examples of $C_2$-$C_{12}$ haloalkenyl are: 2,2-dichloropropenyl, 1,2,2-trichloropropenyl.

Examples of $C_2$-$C_{12}$ alkynyl are propargyl, 2-butynyl.

Examples of $C_3$-$C_{1e}$ cycloalkylcarbonyl are cyclopropanoyl, cyclopentanoyl.

Examples of $C_3$-$C_{18}$ cycloalkylthiocarbonyl are cyclopropylthiocarbonyl, cyclopentylthiocarbonyl.

Examples of $C_3$-$C_{18}$ cycloalkoxycarbonyl are cyclopropoxycarbonyl, cyclohexyloxycarbonyl.

Examples of $C_1$-$C_{12}$ alkoxyls are methoxyl, ethoxyl.

Examples of $C_1$-$C_{12}$ haloalkoxyls are trifluoromethoxyl, 1,1,2,2-tetrafluoroethoxyl, 1,1,2,3,3,3-hexafluoro-propyloxyl.

Examples of $C_3$-$C_{18}$ cycloalkyls are cyclopropoxyl, cyclopentoxyl.

Examples of $R^3R^4R^5Si$ groups are trimethylsilyl, triethylsilyl, dimethyl-t-butylsilyl, dimethyl-phenylsilyl, respectively.

Aryls refer to mono, bi or tricyclic aromatic systems, composed of carbon atoms only, such as for example: phenyl, naphthyl, phenanthrenyl, anthracenyl.

All the aryl, benzyl systems can be substituted by one or more groups selected from halogens, $C_1$-$C_{12}$ alkyls, $C_1$-$C_{12}$ haloalkyls, $C_3$-$C_{18}$ cycloalkyls, $C_1$-$C_{12}$ alkoxyls, $C_4$-$C_{18}$ cycloalkoxyls, $C_1$-$C_{18}$ haloalkoxyls.

Also included in the present invention are:
a) any possible stereoisomers of the compounds having general formula (I) deriving from particular meanings of the substituents R, $R^1$-$R^5$, Ra, Rb, Rc, Z, Q and G;
b) the salts of the compounds having formula (I), obtained for example by the addition of inorganic or organic acids;
c) any possible hydrates of the compounds having formula (I).

Specific examples of compounds having general formula (I) which are interesting for their herbicidal activity are compounds wherein R, $R_1$, $R_2$, Z, n, Q and G have the meanings indicated in Table 1:

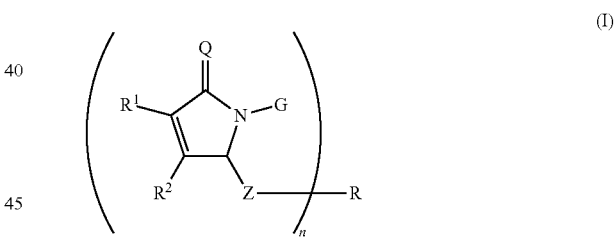

TABLE 1

| Comp. No | $R^1$ | $R^2$ | Z | n | R | Q | G |
|---|---|---|---|---|---|---|---|
| 1 | CH₃ | CH₃ | O | 1 | 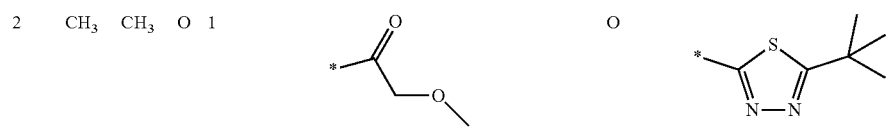 | O | |
| 2 | CH₃ | CH₃ | O | 1 | | O | |

TABLE 1-continued
| Comp. No | R¹ | R² | Z | n | R | Q | G |
|---|---|---|---|---|---|---|---|
| 3 | CH₃ | CH₃ | O | 1 | 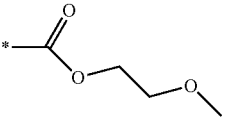 | O | 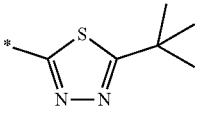 [SMILES: *c1nnc(C(C)(C)C)s1] |
| 4 | CH₃ | CH₃ | O | 1 | 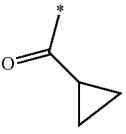 | O | 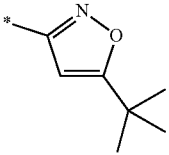 [SMILES: *c1cc(C(C)(C)C)on1] |
| 5 | CH₃ | CH₃ | O | 1 | 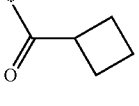 | O | 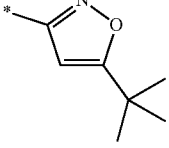 |
| 6 | CH₃ | CH₃ | O | 1 | 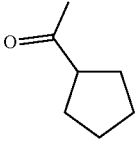 | O | 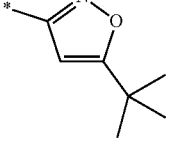 |
| 7 | CH₃ | CH₃ | O | 1 | 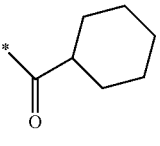 [SMILES: *C(=O)C1CCCCC1] | O | 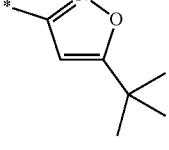 |
| 8 | CH₃ | CH₃ | O | 1 | 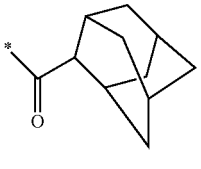 [SMILES: *C(=O)C1C2CC3CC(C2)CC1C3] | O | 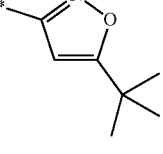 |
| 9 | CH₃ | CH₃ | O | 1 | 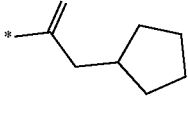 | O | 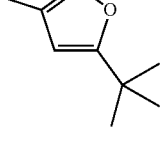 |
| 10 | CH₃ | CH₃ | O | 1 | 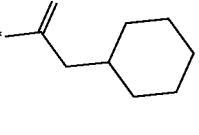 | O | 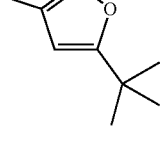 |
| 11 | CH₃ | CH₃ | O | 2 | 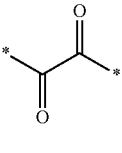 [SMILES: *C(=O)C(*)=O] | O | 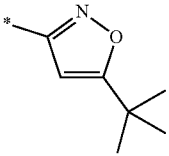 [SMILES: *c1cc(C(C)(C)C)on1] |

TABLE 1-continued

| Comp. No | R¹ | R² | Z | n | R | Q | G |
|---|---|---|---|---|---|---|---|
| 12 | CH₃ | CH₃ | O | 1 | methyl 2-oxoacetate group | O | 5-tert-butylisoxazol-3-yl |
| 13 | CH₃ | CH₃ | O | 1 | methyl 3-oxopropanoate group | O | 5-tert-butylisoxazol-3-yl |
| 14 | CH₃ | CH₃ | O | 1 | 2-methoxyacetyl group | O | 5-tert-butylisoxazol-3-yl |
| 15 | CH₃ | CH₃ | O | 1 | menthyl carbonyl group | O | 5-tert-butylisoxazol-3-yl |
| 16 | CH₃ | CH₃ | O | 2 | malonyl group | O | 5-tert-butylisoxazol-3-yl |
| 17 | CH₃ | CH₃ | O | 1 | cyclopentyloxycarbonyl group | O | 5-tert-butylisoxazol-3-yl |
| 18 | CH₃ | CH₃ | O | 1 | 2-methoxyethoxycarbonyl group | O | 5-tert-butylisoxazol-3-yl |
| 19 | CH₃ | CH₃ | O | 1 | benzyloxycarbonyl group | O | 5-tert-butylisoxazol-3-yl |
| 20 | CH₃ | CH₃ | O | 1 | menthyloxycarbonyl group | O | 5-tert-butylisoxazol-3-yl |

TABLE 1-continued

| Comp. No | R¹ | R² | Z | n | R | Q | G |
|---|---|---|---|---|---|---|---|
| 21 | CH₃ | CH₃ | O | 2 | *-C(=O)-O-CH₂CH₂-O-C(=O)-* | O | 3-*-5-tert-butyl-isoxazole |
| 22 | CH₃ | CH₃ | O | 1 | *-Si(CH₃)₃ | O | 3-*-5-tert-butyl-isoxazole |
| 23 | CH₃ | CH₃ | O | 2 | *-Si(CH₃)₂-CH₂CH₂-Si(CH₃)₂-* | O | 3-*-5-tert-butyl-isoxazole |
| 24 | CH₃ | CH₃ | O | 1 | *-CH₂CH₂-O-CH₃ | O | 3-*-5-tert-butyl-isoxazole |
| 25 | CH₃ | CH₃ | O | 1 | *-CH₂-S-CH₃ | O | 3-*-5-tert-butyl-isoxazole |
| 26 | CH₃ | CH₃ | O | 1 | *-CH₂-C(=O)-CH₃ | O | 3-*-5-tert-butyl-isoxazole |
| 27 | CH₃ | CH₃ | O | 1 | *-CH₂-C(=O)-O-CH₂CH₃ | O | 3-*-5-tert-butyl-isoxazole |
| 28 | CH₃ | CH₃ | O | 1 | *-CH(CH₃)-C(=O)-O-CH₃ | O | 3-*-5-tert-butyl-isoxazole |
| 29 | CH₃ | CH₃ | O | 1 | *-C(=O)-cyclobutyl | O | 2-*-5-CF₃-thiazole |
| 30 | CH₃ | CH₃ | O | 1 | *-C(=O)-CH₂-O-CH₃ | O | 2-*-5-CF₃-thiazole |

TABLE 1-continued
| Comp. No | R¹ | R² | Z | n | R | Q | G |
|---|---|---|---|---|---|---|---|
| 31 | CH₃ | Br | O | 1 | 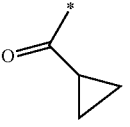 | O | 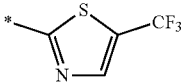 |
| 32 | Br | CH₃ | O | 1 | 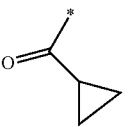 | O | 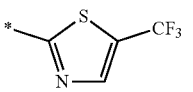 |
| 33 | CH₃ | CH₃ | O | 1 | 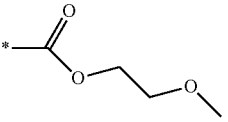 [SMILES: *C(=O)OCCOC] | O | 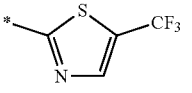 |
| 34 | CH₃ | CH₃ | O | 1 | 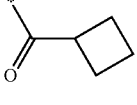 | O | 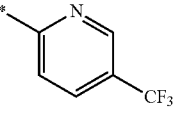 |
| 35 | CH₃ | CH₃ | O | 1 | 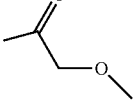 | O | 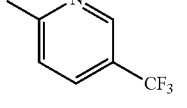 |
| 36 | Cl | CH₃ | O | 1 | 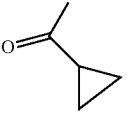 | O | 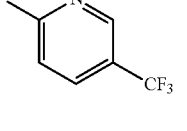 |
| 37 | OCH₃ | CH₃ | O | 1 | 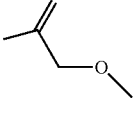 | O | 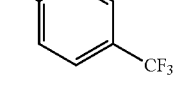 |
| 38 | CH₃ | CH₃ | O | 1 | 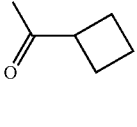 | O | 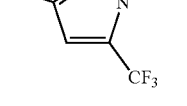 |
| 39 | CH₃ | CH₃ | O | 1 | 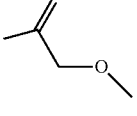 | O | 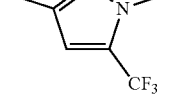 |
| 40 | CH₃ | CH₃ | O | 1 | 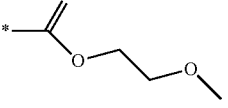 | O | 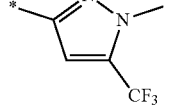 |
| 41 | CH₃ | CH₃ | O | 1 | 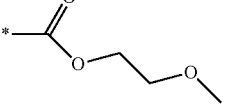 | O | 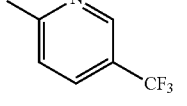 |

TABLE 1-continued
| Comp. No | R¹ | R² | Z | n | R | Q | G |
|---|---|---|---|---|---|---|---|
| 42 | CH₃ | CH₃ | O | 1 | 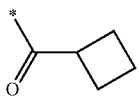 [SMILES: *C(=O)C1CCC1] | O | 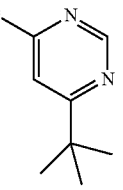 |
| 43 | CH₃ | CH₃ | O | 1 | 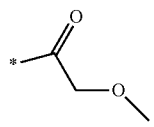 [SMILES: *C(=O)COC] | O | 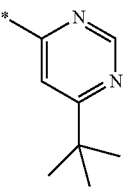 [SMILES: *c1cc(C(C)(C)C)ncn1] |
| 44 | CH₃ | CH₃ | O | 1 | 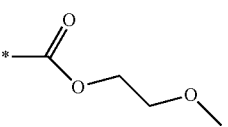 [SMILES: *C(=O)OCCOC] | O | 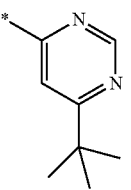 [SMILES: *c1cc(C(C)(C)C)ncn1] |
| 45 | OCH₃ | CH₃ | O | 1 | 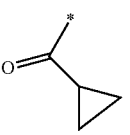 | O | 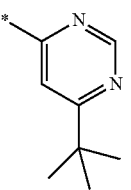 [SMILES: *c1cc(C(C)(C)C)ncn1] |
| 46 | OCH₃ | CH₃ | O | 1 | 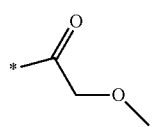 | O | 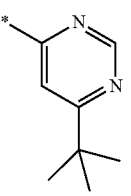 [SMILES: *c1cc(C(C)(C)C)ncn1] |
| 47 | OCH₃ | CH₃ | O | 1 | 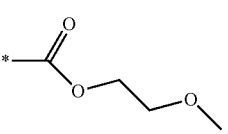 [SMILES: *C(=O)OCCOC] | O | 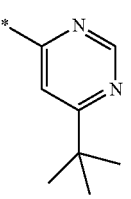 [SMILES: *c1cc(C(C)(C)C)ncn1] |
| 48 | CH₃ | CH₃ | O | 1 | 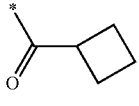 | O | 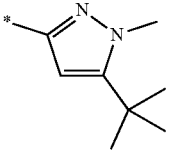 [SMILES: *c1cc(C(C)(C)C)n(C)n1] |
| 49 | CH₃ | CH₃ | O | 1 | 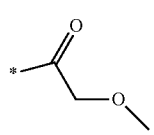 | O | 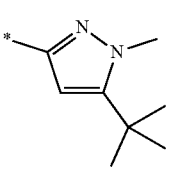 [SMILES: *c1cc(C(C)(C)C)n(C)n1] |

TABLE 1-continued

| Comp. No | R¹ | R² | Z | n | R | Q | G |
|---|---|---|---|---|---|---|---|
| 50 | CH₃ | CH₃ | O | 1 | (acetyl-2-methoxyethyl ester) | O | (1-methyl-5-tert-butyl-pyrazol-3-yl) |
| 51 | CH₃ | Cl | O | 1 | (cyclopropyl ketone) | O | (1-methyl-5-tert-butyl-pyrazol-3-yl) |
| 52 | CH₃ | Cl | O | 1 | (methoxymethyl ketone) | O | (1-methyl-5-tert-butyl-pyrazol-3-yl) |
| 53 | CH₃ | Cl | O | 1 | (2-methoxyethyl ester) | O | (1-methyl-5-tert-butyl-pyrazol-3-yl) |
| 54 | Cl | CH₃ | O | 1 | (cyclopropyl ketone) | O | (1-methyl-5-tert-butyl-pyrazol-3-yl) |
| 55 | Cl | CH₃ | O | 1 | (methoxymethyl ketone) | O | (1-methyl-5-tert-butyl-pyrazol-3-yl) |
| 56 | Cl | CH₃ | O | 1 | (2-methoxyethyl ester) | O | (1-methyl-5-tert-butyl-pyrazol-3-yl) |
| 57 | OCH₃ | CH₃ | O | 1 | (cyclopropyl ketone) | O | (5-tert-butyl-1,3,4-thiadiazol-2-yl) |
| 58 | OCH₃ | CH₃ | O | 1 | (methoxymethyl ketone) | O | (5-tert-butyl-1,3,4-thiadiazol-2-yl) |
| 59 | OCH₃ | CH₃ | O | 1 | (2-methoxyethyl ester) | O | (5-tert-butyl-1,3,4-thiadiazol-2-yl) |

TABLE 1-continued
| Comp. No | R¹ | R² | Z | n | R | Q | G |
|---|---|---|---|---|---|---|---|
| 60 | Cl | CH₃ | O | 1 | 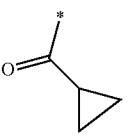 | O | 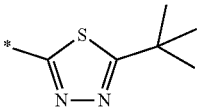 [SMILES: *c1nnc(C(C)(C)C)s1] |
| 61 | Cl | CH₃ | O | 1 | 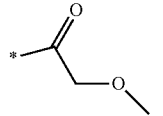 | O | 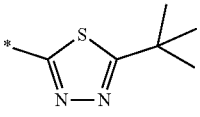 [SMILES: *c1nnc(C(C)(C)C)s1] |
| 62 | Cl | CH₃ | O | 1 | 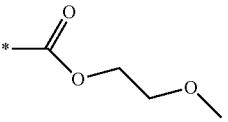 [SMILES: *C(=O)OCCOC] | O | 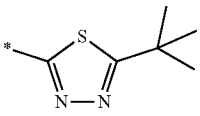 [SMILES: *c1nnc(C(C)(C)C)s1] |
| 63 | OCH₃ | CH₃ | O | 1 | 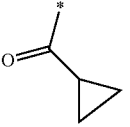 [SMILES: *C(=O)C1CC1] | O | 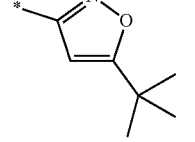 |
| 64 | OCH₃ | CH₃ | O | 1 | 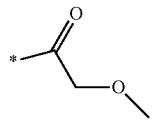 | O | 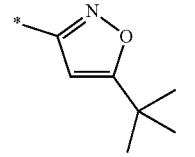 [SMILES: *c1cc(C(C)(C)C)on1] |
| 65 | OCH₃ | CH₃ | O | 1 | 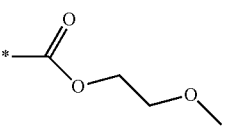 [SMILES: *C(=O)OCCOC] | O | 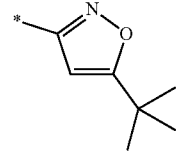 [SMILES: *c1cc(C(C)(C)C)on1] |
| 66 | Cl | CH₃ | O | 1 | 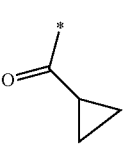 | O | 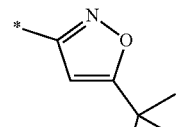 |
| 67 | Cl | CH₃ | O | 1 | 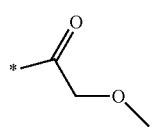 | O | 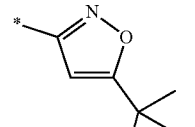 |
| 68 | Cl | CH₃ | O | 1 | 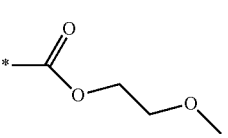 [SMILES: *C(=O)OCCOC] | O | 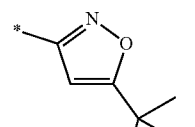 |
| 69 | OCH₃ | CH₃ | O | 1 | 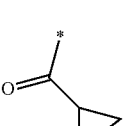 | O | 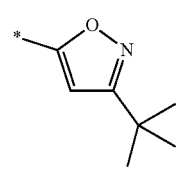 [SMILES: *c1cc(C(C)(C)C)no1] |

TABLE 1-continued

| Comp. No | R¹ | R² | Z | n | R | Q | G |
|---|---|---|---|---|---|---|---|
| 70 | OCH₃ | CH₃ | O | 1 | cyclopropyl-C(=O)-* | O | *-oxazole-5-C(CH₃)₃ |
| 71 | OCH₃ | CH₃ | O | 1 | cyclopropyl-C(=O)-* | O | *-1,3,4-oxadiazole-5-C(CH₃)₃ |
| 72 | CH₃ | CH₃ | O | 1 | cyclopropyl-C(=O)-* | O | *-isoxazole-3-C(CH₃)₃ |
| 73 | CH₃ | CH₃ | O | 1 | cyclopropyl-C(=O)-* | O | *-oxazole-5-C(CH₃)₃ |
| 74 | CH₃ | CH₃ | O | 1 | cyclopropyl-C(=O)-* | O | *-1,3,4-oxadiazole-5-C(CH₃)₃ |
| 75 | Cl | CH₃ | O | 1 | cyclopropyl-C(=O)-* | O | *-isoxazole-3-C(CH₃)₃ |
| 76 | Cl | CH₃ | O | 1 | cyclopropyl-C(=O)-* | O | *-oxazole-5-C(CH₃)₃ |
| 77 | Cl | CH₃ | O | 1 | cyclopropyl-C(=O)-* | O | *-1,3,4-oxadiazole-5-C(CH₃)₃ |
| 78 | CH₃ | CH₃ | O | 1 | cyclopropyl-C(=O)-* | NOH | *-isoxazole-5-C(CH₃)₃ |

TABLE 1-continued
| Comp. No | R¹ | R² | Z | n | R | Q | G |
|---|---|---|---|---|---|---|---|
| 79 | Cl | CH₃ | O | 1 | 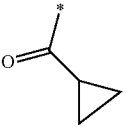 | NOH | 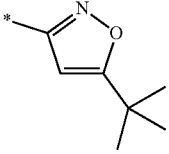 [SMILES: *c1cc(C(C)(C)C)on1] |
| 80 | OCH₃ | CH₃ | O | 1 | 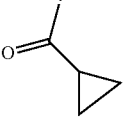 | NOH | 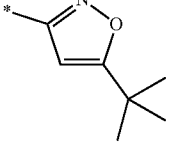 |
| 81 | Br | CH₃ | O | 1 | 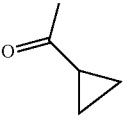 | NOH | 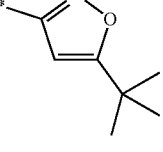 |
| 82 | CH₃ | CH₃ | O | 1 | 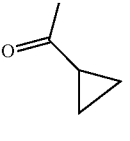 | NOCH₃ | 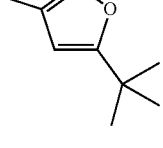 |
| 83 | CH₃ | CH₃ | O | 1 | 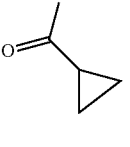 | N(CH₃)₂ | 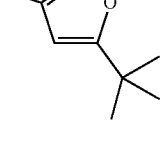 |
| 84 | CH₃ | CH₃ | S | 1 | 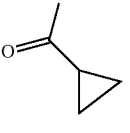 | O | 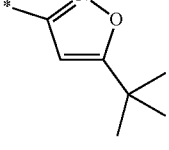 |
| 85 | Cl | CH₃ | S | 1 | 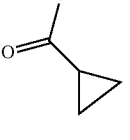 | O | 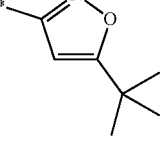 |
| 86 | OCH₃ | CH₃ | S | 1 | 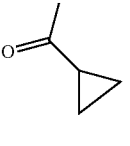 | O | 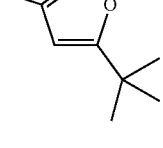 |
| 87 | CH₃ | CH₃ | O | 1 | 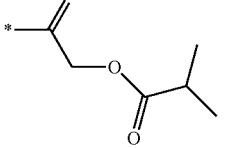 | O | 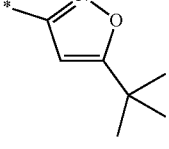 |

TABLE 1-continued
| Comp. No | R¹ | R² | Z | n | R | Q | G |
|---|---|---|---|---|---|---|---|
| 88 | CH₃ | CH₃ | O | 1 | 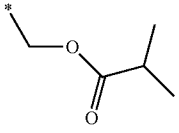 | O | 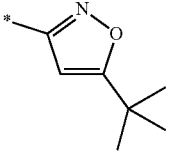 [SMILES: *c1cc(C(C)(C)C)on1] |
| 89 | CH₃ | CH₃ | O | 1 | 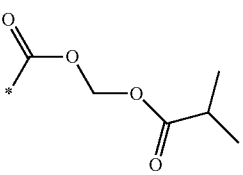 [SMILES: *C(=O)OCOC(=O)C(C)C] | O | 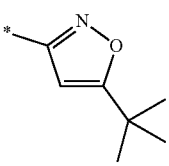 [SMILES: *c1cc(C(C)(C)C)on1] |
| 90 | CH₃ | CH₃ | O | 1 | 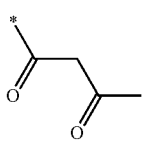 | O | 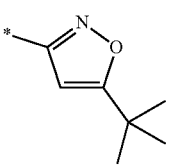 |
| 91 | CH₃ | CH₃ | S | 1 | 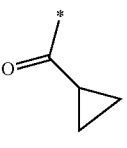 [SMILES: *C(=O)C1CC1] | S | 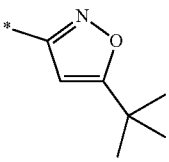 [SMILES: *c1cc(C(C)(C)C)on1] |
| 92 | Cl | CH₃ | S | 1 | 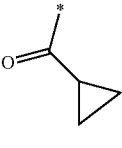 | S | 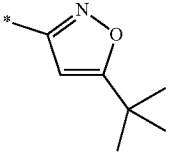 [SMILES: *c1cc(C(C)(C)C)on1] |
| 93 | OCH₃ | CH₃ | S | 1 | 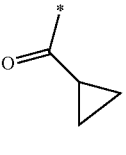 | S | 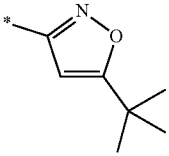 [SMILES: *c1cc(C(C)(C)C)on1] |
| 94 | CH₃ | CH₃ | O | 1 | 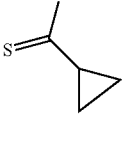 | S | 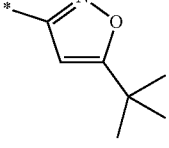 |
| 95 | Cl | CH₃ | O | 1 | 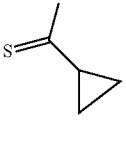 | S | 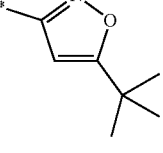 |
| 96 | OCH₃ | CH₃ | O | 1 | 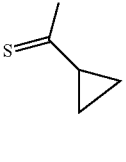 | S | 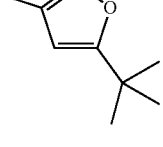 |

TABLE 1-continued
| Comp. No | R$^1$ | R$^2$ | Z | n | R | Q | G |
|---|---|---|---|---|---|---|---|
| 97 | CH$_3$ | CH$_3$ | S | 1 | 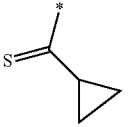 [SMILES: *C(=S)C1CC1] | S | 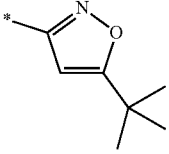 [SMILES: *c1cc(C(C)(C)C)on1] |
| 98 | Cl | CH$_3$ | S | 1 | 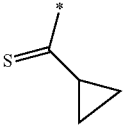 | S | 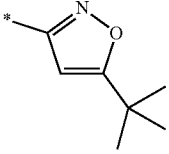 |
| 99 | OCH$_3$ | CH$_3$ | S | 1 | 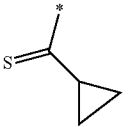 | S | 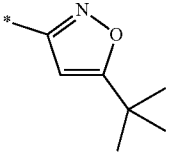 [SMILES: *c1cc(C(C)(C)C)on1] |
| 100 | CH$_3$ | CH$_3$ | O | 1 | 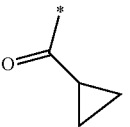 [SMILES: *C(=O)C1CC1] | O | 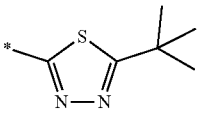 [SMILES: *c1nnc(C(C)(C)C)s1] |
| 101 | CH$_3$ | CH$_3$ | O | 1 | 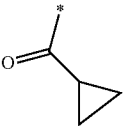 [SMILES: *C(=O)C1CC1] | O | 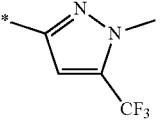 |
| 102 | CH$_3$ | CH$_3$ | O | 1 | 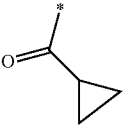 | O | 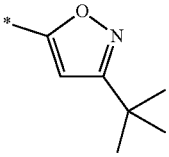 [SMILES: *c1cc(C(C)(C)C)no1] |
| 103 | CH$_3$ | CH$_3$ | O | 1 | 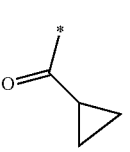 | O | 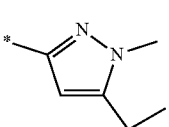 |
| 104 | CH$_3$ | CH$_3$ | O | 1 | 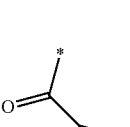 | O | 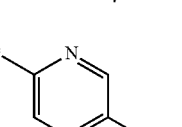 |
| 105 | CH$_3$ | CH$_3$ | O | 1 | 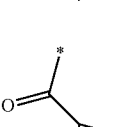 | O | 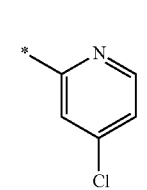 [SMILES: *c1cc(Cl)ccn1] |

TABLE 1-continued
| Comp. No | R¹ | R² | Z | n | R | Q | G |
|---|---|---|---|---|---|---|---|
| 106 | CH₃ | CH₃ | O | 1 | 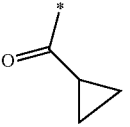 [SMILES: *C(=O)C1CC1] | O | 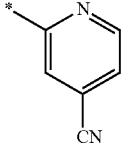 [SMILES: *c1cc(C#N)ccn1] |
| 107 | CH₃ | CH₃ | O | 1 | 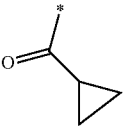 [SMILES: *C(=O)C1CC1] | O | 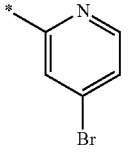 [SMILES: *c1cc(Br)ccn1] |
| 108 | CH₃ | CH₃ | O | 1 | 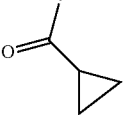 | O | 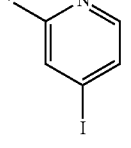 |
| 109 | CH₃ | CH₃ | O | 1 | 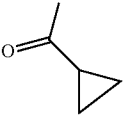 | O | 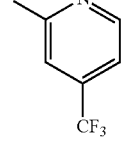 |
| 110 | CH₃ | CH₃ | O | 1 | 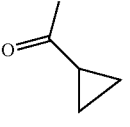 | O | 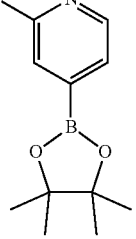 |
| 111 | CH₃ | CH₃ | O | 1 | 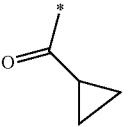 | O | 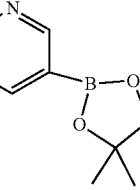 |
| 112 | CH₃ | CH₃ | O | 1 | 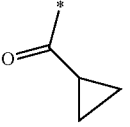 | O | 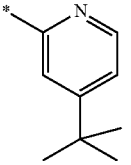 |
| 113 | CH₃ | CH₃ | O | 1 | 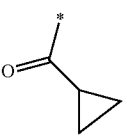 [SMILES: *C(=O)C1CC1] | O | 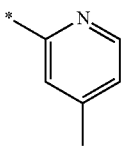 [SMILES: *c1cc(C)ccn1] |

TABLE 1-continued

| Comp. No | R¹ | R² | Z | n | R | Q | G |
|---|---|---|---|---|---|---|---|
| 114 | CH₃ | CH₃ | O | 1 | *-C(=O)-CH₂CH₂CH₂CH₂CH₂CH₂CH₃ (octanoyl) | O | 3-*-5-tert-butyl-isoxazolyl |
| 115 | CH₃ | CH₃ | O | 1 | *-C(=O)-CH₂CH₂-CH=CF₂ | O | 3-*-5-tert-butyl-isoxazolyl |
| 116 | CH₃ | CH₃ | O | 1 | *-C(=O)-CH₂-CH=CF₂ (with one F on terminal C) | O | 3-*-5-tert-butyl-isoxazolyl |
| 117 | CH₃ | CH₃ | O | 1 | *-C(=O)-CH₂CH₂-O-CH₃ | O | 2-*-5-tert-butyl-1,3,4-thiadiazolyl |
| 118 | CH₃ | CH₃ | O | 1 | *-C(=O)-CH₂CH₂CH₂-O-CH₃ | O | 2-*-5-tert-butyl-1,3,4-thiadiazolyl |
| 119 | CH₃ | CH₃ | O | 1 | *-C(=O)-cyclopropyl | O | 4-*-6-tert-butyl-pyrimidinyl |

Compounds having formula (I) preferred for their biological activity are those wherein:
  R represents a group selected from a $C_3$-$C_{12}$ cycloalkylcarbonyl group, a $C_1$-$C_{18}$ alkoxyalkylcarbonyl group, a $C_1$-$C_{18}$alkoxy$C_1$-$C_{18}$alkoxycarbonyl group, a $R^3R^4R^5$Si group or a —(COCO)— group,
  Z represents an oxygen or sulfur atom,
  Q represents an oxygen atom or an NOH group,
  $R^1$ and $R^2$ the same as each other represent a $C_1$-$C_4$ alkyl,
  n is equal to 1 or 2 and
  G is selected from $G^1$ to $G^6$ and represents a hexa- or penta-atomic heterocyclic ring containing at least one heteroatom selected from nitrogen, oxygen and sulfur.

Even more preferred are compounds having formula (I) wherein:
  R represents a group selected from a cyclopropylcarbonyl group, a methoxymethylcarbonyl group, a methoxyethoxycarbonyl group, a trimethylsilyl group or a —(COCO)— group,
  $R^1$ and $R^2$ are methyl or ethyl,
  Z and Q represent an oxygen atom,
  n is equal to 1 or 2 and
  G is selected from $G^1$ to $G^4$ and represents a thiadiazolyl, an isoxazolyl or a pyrazolyl group.

Particularly preferred are compounds having general formula (I) wherein R, $R^1$, $R^2$, Z, Q, G and n have the meanings indicated in Table 2.

TABLE 2
| Comp. No | R¹ | R² | Z | n | R | Q | G |
|---|---|---|---|---|---|---|---|
| 2 | CH₃ | CH₃ | O | 1 | 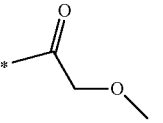 | O | 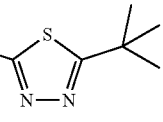 |
| 3 | CH₃ | CH₃ | O | 1 | 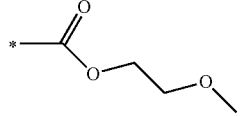 | O | 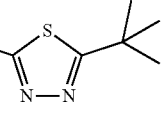 |
| 4 | CH₃ | CH₃ | O | 1 | 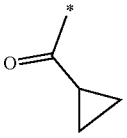 | O | 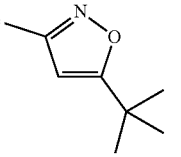 |
| 11 | CH₃ | CH₃ | O | 2 | 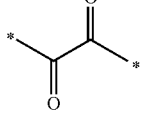 | O | 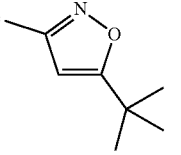 |
| 14 | CH₃ | CH₃ | O | 1 | 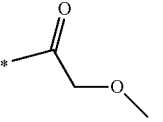 | O | 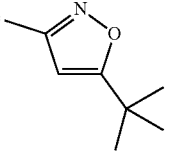 |
| 18 | CH₃ | CH₃ | O | 1 | 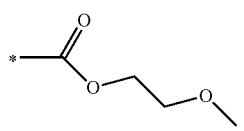 | O | 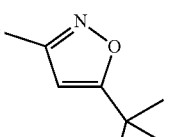 |
| 22 | CH₃ | CH₃ | O | 1 |  | O | 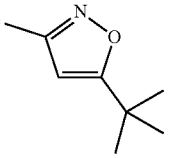 |
| 100 | CH₃ | CH₃ | O | 1 | 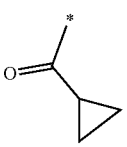 | O | 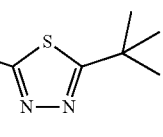 |
| 101 | CH₃ | CH₃ | O | 1 | 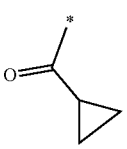 | O | 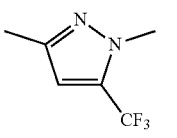 |

TABLE 2-continued
| Comp. No | R¹ | R² | Z | n | R | Q | G |
|---|---|---|---|---|---|---|---|
| 109 | CH₃ | CH₃ | O | 1 | 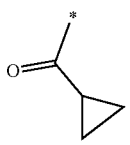 | O | 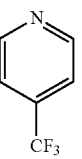 |
| 110 | CH₃ | CH₃ | O | 1 | 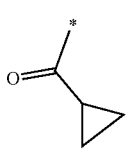 | O | 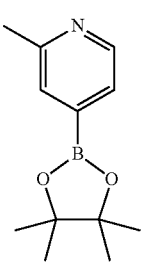 |
| 113 | CH₃ | CH₃ | O | 1 | 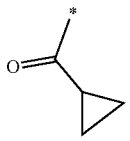 | O | 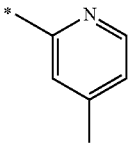 |
| 114 | CH₃ | CH₃ | O | 1 | 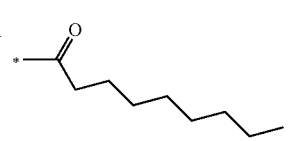 | O | 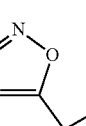 |
| 117 | CH₃ | CH₃ | O | 1 | 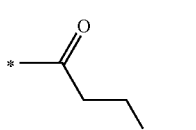 | O | 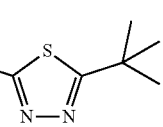 |
| 118 | CH₃ | CH₃ | O | 1 | 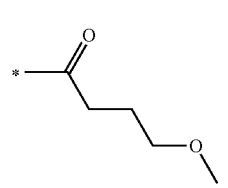 | O | 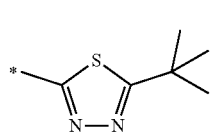 |
| 119 | CH₃ | CH₃ | O | 1 | 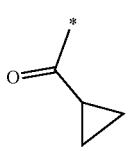 | O | 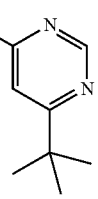 |

As will be clear to skilled persons in the field, the compounds having general formula (I), can be obtained in the form of two or more optical isomers.

An object of the present invention therefore relates to compounds having general formula (I) in racemic form, isomerically pure or their mixtures, possibly obtained during the preparation of the compounds having general formula (I) or deriving from an incomplete separation of the same isomers, in any proportion.

A further object of the present invention relates to a process for the preparation of compounds having general formula (I).

In particular, the compounds having general formula (I) can be prepared from the corresponding compound having formula (II) by functionalization of the ZH group with a compound R-T having formula (III), wherein R has the meanings previously indicated, as shown in reaction scheme 1.

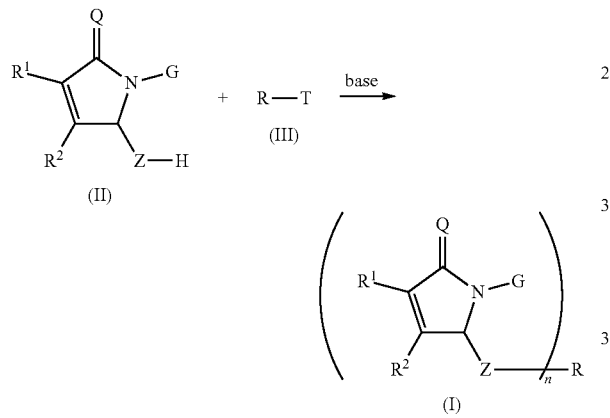

More specifically, when n has the values of 1 or 2, the reaction can provide for the treatment of the compound having formula (II) with a compound R-T having formula (III) in the presence of an organic or inorganic base, in a suitable solvent, wherein, in said formula (III), T represents an leaving group, such as for example a halogen selected from Cl, Br, I, or a mesylate, p-toluenesulfonate or trifluoromethanesulfonate group. The compound having formula (III) can be obtained as described, for example, in Theodora W. Greene "Protective Groups in Organic Synthesis" Third Edition pages 198-199. The above-mentioned organic or inorganic base can, for example, be: triethylamine, pyridine, sodium acetate, sodium or potassium hydride, potassium or calcium bicarbonate, sodium or potassium hydroxide. The above-mentioned solvent can, for example, be: dichloroethane, chloroform or methylene chloride, tetrahydrofuran. The above reaction can be carried out, for example, at a temperature ranging from 0° C. to the reflux temperature of the solvent selected.

The compound having formula (II), when Z and Q have the meaning of oxygen, can be prepared by reduction of the corresponding precursor (IV) as indicated in reaction scheme 2, using, for example, as a reducing agent, sodium borohydride or lithium aluminium hydride, in a suitable alcohol solvent (e.g. methanol, ethanol, propanol, isopropanol) or in a halogenated hydrocarbon solvent (e.g. dichloromethane, dichloroethane or chloroform or in ethers such as dioxane or tetrahydrofuran.

The reaction can conveniently be carried out at a temperature ranging from 0° C. to room temperature, for a time ranging from 1 to 12 hours.

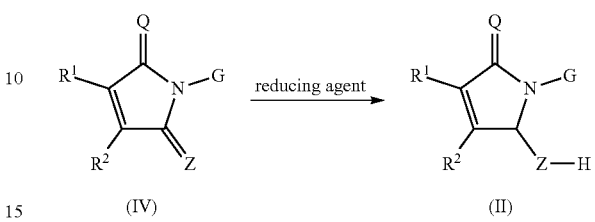

The compound having formula (II), when Z represents an S atom or a NR$^4$ group and Q is oxygen, can be prepared starting from compound (V), wherein T represents an leaving group, such as for example a halogen selected from Cl, Br, I, or a mesylate, p-toluenesulfonate or trifluoromethanesulfonate group, by substitution with an amine having formula R$^4$NH$_2$ or a salt, such as KSH or NaSH, as indicated in reaction scheme 3 and as described in literature, for example in EP0297378 and in EP0339390.

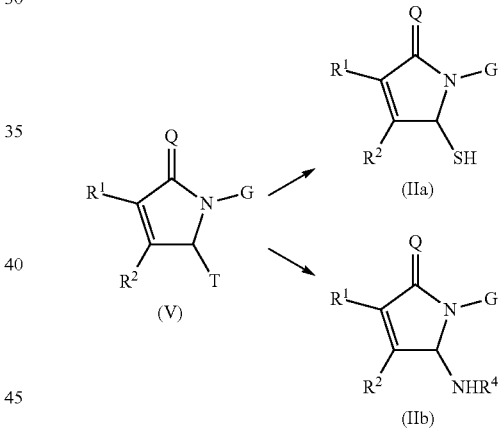

Alternatively, the compounds having general formula (I), when Z represents an oxygen atom, can be obtained by reaction of a compound having formula (VI) (wherein T represents an leaving group such as for example a halogen selected from Cl, Br, I, or a mesylate, p-toluenesulfonate or trifluoromethanesulfonate) group with an compound R—ZH having formula (VII), according to reaction scheme 4.

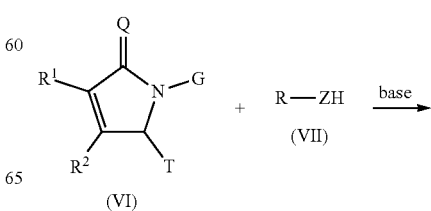

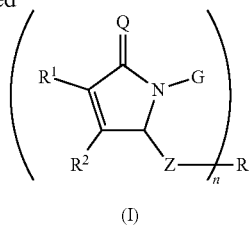

The reaction can be carried out in the presence of an organic or inorganic base (for example: triethylamine, pyridine, sodium acetate, sodium or potassium hydride, potassium or calcium bicarbonate, sodium or potassium hydroxide), in a suitable solvent (e.g. dichloroethane, chloroform, methylene chloride or tetrahydrofuran), at a temperature ranging from 0° C. to the reflux temperature of the solvent selected, and generally within the range of 0° C.-90° C., as described for example in Plouvier, B et al. "Journal Medicinal Chemistry", 2007, vol. 50, pages 2818-2841 or in Campbell S. et al. "Journal of Medicinal Chemistry, 1988, vol. 31, pages 516-520 or in Kyasa S. et al. "Journal of Organic Chemistry", 2015, vol. 80, pages 12100-12114.

The compound having formula (IV), when Q and Z have the meaning of oxygen, can be prepared by reaction of the appropriate maleic anhydride (VIII) with a compound G-NH$_2$ having formula (IX), with G having the meanings of G$^1$-G$^6$, in an acidic environment (for example, glacial acetic acid), in the presence or absence of a solvent, at a temperature ranging from 0° C. to the reflux temperature of the solvent used, and in general within the range of 0° C.-90° C., as indicated in reaction scheme 5 and as described for example in EP0297378 or in EP0286816, Scheme 5

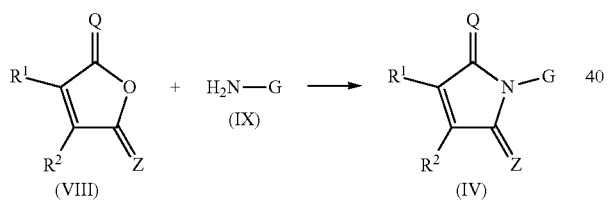

Alternatively, the compounds having general formula (IV), when Q and Z have the meaning of oxygen, can be obtained by reaction of the appropriate maleic imide (X) with a compound TG having general formula (XI), wherein G has the meanings of G$^1$-G$^6$ and T is an leaving group that has the meanings indicated above, as described, for example, in Wolfe R M W et al. "Organic Letters" 2017, vol. 19 pages 996-999 and according to what is indicated in reaction scheme 6.

Scheme 6

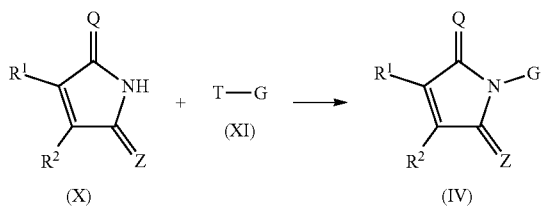

Alternatively, the compounds having general formula (II) wherein Q and Z represent an oxygen atom, can be obtained by reaction of the suitable hydroxypyrrolone (XII) with a compound TG having general formula (XI), wherein T represents a halogen atom selected from Cl, Br, I, and G the meanings of G$^1$-G$^6$, in the presence of a transition metal complex (for example, Pd$_2$(dba)$_3$ (tris(dibenzylideneacetone)dipalladium(0)) or Pd(OAc)$_2$ (Pd (II) acetate), possibly in the presence of a ligand such as, for example, Xantphos or Brettphos), in the presence o absence of a base (for example, potassium carbonate or cesium carbonate) and in an inert solvent (e.g. toluene or dioxane), as described in literature, for example, in Yin J. et al. "Organic. Letters", Vol. 2, No. 8, 2000, 1101-1104, according to reaction scheme 7.

Scheme 7

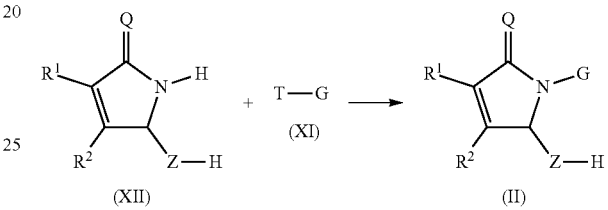

The compounds having formula (IV), when Q and Z have the meanings of oxygen and when R$^1$ and R$^2$ are different from each other and have the meaning of a halogen atom such as Cl or Br, can be easily obtained according to methods well-known in organic chemistry, e.g. by halogenation reaction of the intermediate (XIII) using Alg$_2$ as reagent, wherein Alg is for example Br or Cl according to reaction scheme 8, as described for example in WO2014180740.

Scheme 8

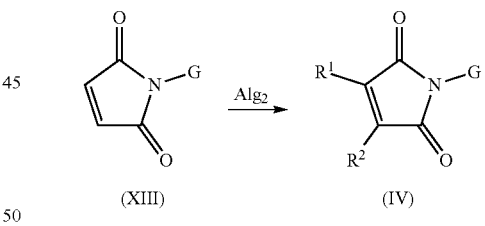

The hydroxypyrrolones having formula (II), when Q and Z have the meanings of oxygen and when R$^1$ and R$^2$ are different from halogen atom, can be easily obtained by acylation of a compound G-NH$_2$ having formula (IX), with G having the meanings of G$^1$-G$^6$, with a compound having formula (XV)—the latter in turn being obtained from a compound having formula (XIV)—to give a compound having formula (XVI) through reactions known in literature. The compound having formula (XVI) in the presence of the compound having general formula (XVII) can then be converted by Horner-Wadsworth-Emmons reaction into the intermediates (XVIIIa) and (XVIIIb), which cyclize under acidic conditions providing the intermediate having formula (II), according to reaction scheme 9 and as described, for example, in WO2014180740.

Scheme 9

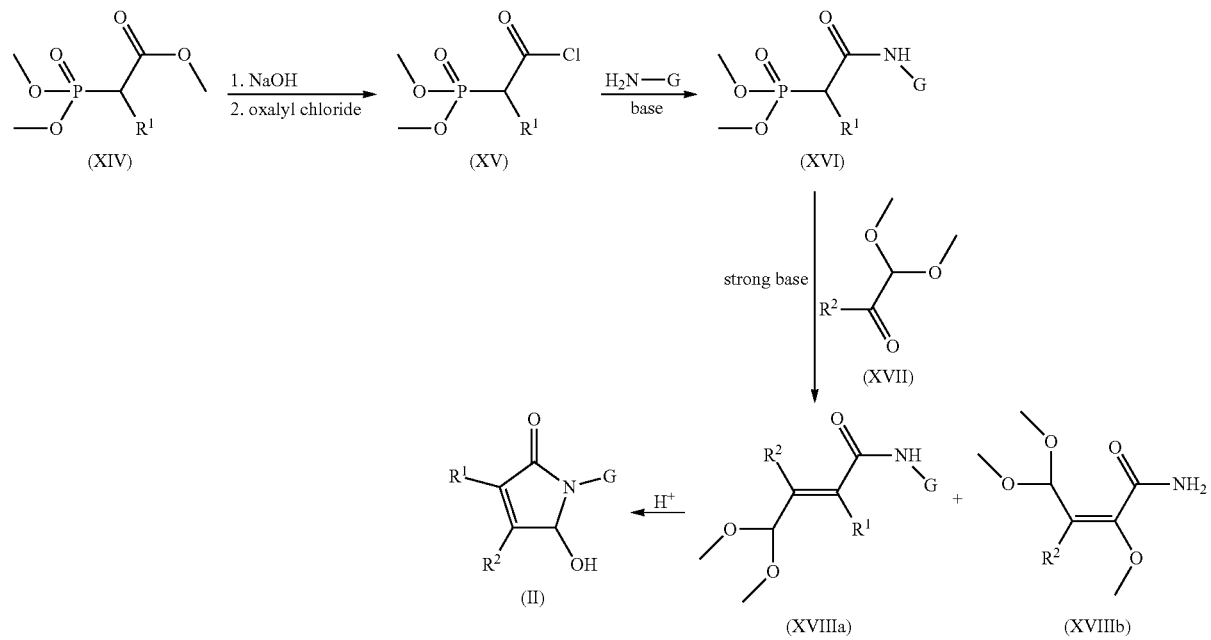

The compounds having general formula (I), when Q has the meaning of S (Ia), can be prepared by reaction of the corresponding compound having general formula (I) wherein Q has the meaning of oxygen, with a suitable reagent, such as, for example, the Lawessons reagent, or diphosphorus pentasulfide, as clearly described in literature, for example in El-Sharief, A. et al. "Indian Journal of Chemistry, Section B: Organic Chemistry Including Medicinal Chemistry", 1981, vol. 20; nb. 9, pages 751-754 or in Psutka K. et al. "RSC Advances", 2016, vol. 6; nb. 82, pages 78784-78790, according to reaction scheme 10.

Scheme 10

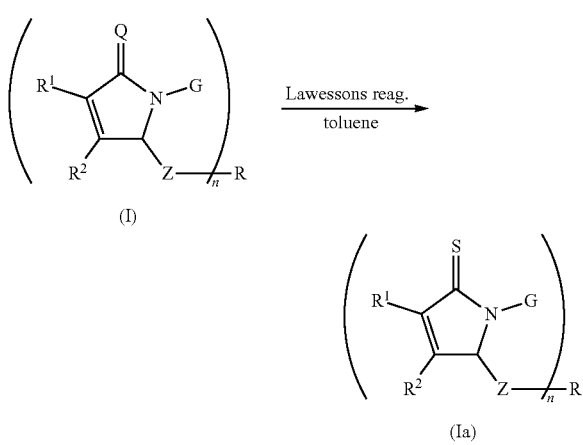

The compounds having general formula (I), when Q has the meaning of NOR$^3$ (Ib), can be prepared by reaction of the compound (Ia) with a reagent having formula NH$_2$OR$^3$ (XIX), as described in literature, for example in Poon Steve F. et al. "Bioorganic and Medicinal Chemistry Letters" (2005), vol. 15; nb. 9; pages 2259-2263, according to reaction scheme 11:

Scheme 11

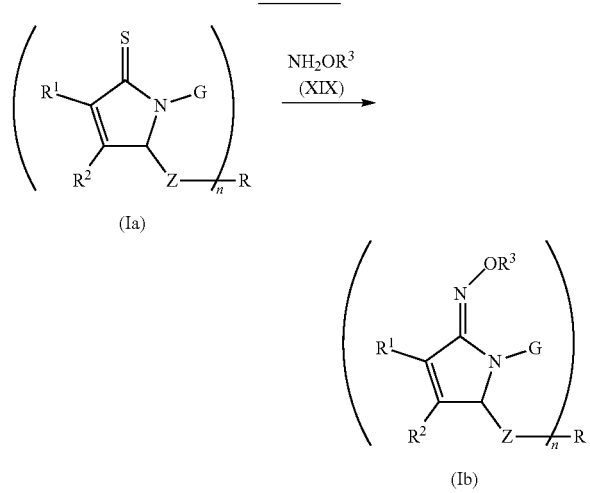

The compounds having general formula (I), when Q has the meaning of CR$^3$R$^4$, can be prepared as described for example in patent application EP403891.

The compounds having general formula (I), when Q has the meaning of NR$^3$R$^4$, can be prepared, for example, by refluxing a solution in toluene of the amine NHR$^3$R$^4$ and the compound having general formula (II) until the complete removal of the water from the reaction medium using a Dean-Stark apparatus or by means of a dehydrating agent, such as, for example, sodium sulfate or by acid catalysis.

The compounds NH$_2$G with G having the meanings of G$^1$-G$^6$ having formula (IX), when they are not commercially available for particular $G^1$-$G^6$ meanings, can be prepared by the methods known in literature, as described for example in Katrizky A. R "Comprehensive Heterocyclic Chemistry: The Structure, Reactions, Synthesis and Uses of Heterocyclic Compounds" 1998, Elsevier Science & Technology Books.

As already indicated, the compounds having general formula (I) are provided with a high herbicidal activity which makes them suitable for use in the agricultural field in the defense of useful crops from weeds.

A further object of the present invention therefore relates to the use of the compounds having general formula (I) in racemic form, isomerically pure or their mixtures, or a composition containing them as herbicides.

In particular, the compounds, object of the present invention, are effective in the control, both in pre-emergence and in post-emergence, of numerous weeds, in particular monocotyledonous and dicotyledonous weeds.

Furthermore, the compounds having general formula (I) can be used in the control of weeds resistant to herbicidal compounds having a different action mechanism, such as for example sulfonylureas, glyphosate or 4-hydroxyphenyl pyruvate-dioxygenase (4-HPPD) inhibitors.

At the same time, in pre- and/or post-emergence treatments, the compounds having general formula (I) can show compatibility or absence of toxic effects with respect to useful crops.

The compounds of the present invention can therefore act both as total herbicides and as selective herbicides, also in relation to the quantity of active ingredient used.

Examples of weeds that can be effectively controlled using compounds having general formula (I) are: *Abutilon theofrasti, Alisma plantago, Amaranthus* spp., *Amni maius, Capsella bursa pastoris, Chenopodium album, Convolvulus sepium, Galium aparine, Geranium dissectum, Heteranthera* spp., *Ipomea* spp., *Matricaria* spp., *Papaver rhoaes, Phaseolus aureus, Polygonum persicaria, Portulaca oleracea, Setaria viridis, Sida spinosa, Sinapsis arvensis, Solanum nigrum, Stellaria media, Veronica* spp., *Viola* spp., *Xanthium* spp., *Alopecurus myosuroides, Anisanta* spp., *Apera spica-venti, Avena* spp., *Cyperus* spp., *Digitaria sanguinalis, Eleusine* spp. *Echinochloa* spp., *Eleocharis avicularis, Lolium* spp., *Panicum* spp., *Poa* spp., *Scirpus* spp., *Sorghum* spp., etc.

At the doses of use effective for agricultural applications, many of the above compounds have not shown toxic effects towards one or more important agricultural crops, such as, for example, wheat (*Triticum* sp.), barley (*Hordeum vulgare*), corn (*Zea mays*), soybean (*Glycine max*).

A further object of the present invention relates to a method for controlling weeds in cultivated areas which comprises the application of an effective dose of at least one compound having general formula (I) or a composition containing it, to the agricultural crops of interest.

The amount of compound to be applied for obtaining the desired effect (effective dose) can vary in relation to various factors such as, for example, the compound used, the crop to be preserved, the weed to be struck, the degree of infestation, the climatic conditions, the characteristics of the soil, the method of application, etc.

Doses of compound ranging from 1 g to 1,000 g per hectare generally provide a sufficient control.

In order to apply at least one compound having general formula (I) as herbicide on a weed or crop, said compound having general formula (I) is formulated in the form of a composition which comprises, in addition to the above-mentioned compound, at least one solvent medium and/or an inert diluent medium. Said inert diluent can be in solid or liquid form. The composition can optionally comprise at least one agronomically acceptable excipient.

A further object of the present invention therefore relates to a herbicide composition comprising at least one compound having general formula (I) in racemic form, isomerically pure or mixtures thereof, at least one inert solvent and/or diluent and optionally at least one agronomically acceptable excipient.

The inert diluents can be solid or liquid. Kaolin, alumina, silica, talc, bentonite, gypsum, quartz, dolomite, attapulgite, montmorillonite, diatomaceous earth, cellulose, starch, etc. or mixtures thereof, can be used, for example, as solid diluents, also called carriers.

Liquid inert diluents that can be used are for example: water, or organic solvents such as aromatic hydrocarbons (xylols, mixtures of alkylbenzenes, etc.), aliphatic hydrocarbons (hexane, cyclohexane, etc.), halogenated aromatic hydrocarbons (chlorobenzene, etc.), alcohols (methanol, propanol, butanol, octanol, etc.), esters (isobutyl acetate, etc.), ketones (acetone, cyclohexanone, acetophenone, isophorone, ethylamylketone, etc.), vegetable oils, mineral oils or mixtures thereof.

Said at least one agronomically acceptable excipient is preferably selected from surfactants, dispersants, stabilizers and mixtures thereof.

Surfactants that can be used are, for example, wetting agents and emulsifiers of the non-ionic type (polyethoxylated alkylphenols, polyethoxylated fatty alcohols, etc.), anionic type (alkylbenzenesulfonates, alkylsulfonates, etc.) or cationic type (quaternary salts of alkylammonium, etc.).

Lignin and its salts, cellulose derivatives, alginates, etc. can also be added, for example, as dispersants.

Antioxidants, ultraviolet ray absorbents, etc. can also be added, for example, as stabilizers.

The formulations suitable for agricultural use can be in the form of: dry powders, wettable powders, emulsifiable concentrates, microemulsions, pastes, granulates, solutions, suspensions, etc., the choice of the type of composition depending on the specific use.

In order to broaden the spectrum of action of the above-mentioned compositions, one or more other active ingredients compatible with the compounds having general formula (I) can be added to the same, such as, for example, herbicides other than compounds having general formula (I), fungicides, insecticides, acaricides, fertilizers, phytoprotectors (safeners), etc.

Examples of herbicides other than compounds having general formula (I) that can be added to the compositions containing at least one compound having general formula (I) in order to broaden the spectrum and possibly give rise to synergistic compositions, are the following:

acetochlor, acifluorfen, aclonifen, alachlor, ametryn, amicarbazone, amidosulfuron, aminocyclopyrachlor, aminopyralid, amitrole, anilofos, asulam, atrazine, azafenidin, azimsulfuron, aziprotryne, beflubutamid, benazolin, bencarbazone, benfluralin, benfuresate, bensulide, bentazone, benzfendizone, benzobicyclon, benzofenap, benzthiazuron, bicyclopyrone, bifenox, bilanafos, bromacil, bromobutide, bromofenoxim, bromoxynil, butachlor, butafenacil, butamifos, butenachlor, butralin, butroxydim, butylate, cafenstrole, carbetamide, carfentrazone-ethyl, chlomethoxyfen, chloramben, chlorbromuron, chlorbufam, chlorflurenol, chloridazon, chlornitrofen, chlorotoluron, chloroxuron, chlorpropham, chlorsulfuron, chlorthal, chlorthiamid, cinidon ethyl, cinmethylin, cinosulfuron, clacyfos, clethodim, clodinafop, clomazone, clomeprop, clopyralid, cloransulam-methyl, cumyluron, cyanazine, cycloate, cyclopyranil, cyclopyrimorate, cyclosulfamuron, cycloxydim, cyhalofop-butyl, cyprosulfamide, 2,4-D, 2,4-DB, daimuron, dalapon, desmedipham, desmetryn, dicamba, dichlobenil, dichlorprop, dichlorprop-P, diclofop, diclosulam, diethatyl, difenoxuron, difenzoquat, diflufenican, diflufenzopyr, dimefuron, dimepiperate, dimethachlor, dimethametryn, dimethenamid, dimethenamid-P dinitramine, dinoseb, dinoseb acetate, dinoterb, diphenamid, dipropetryn, diquat, dithiopyr, 1-diuron, eglinazine, endothal, EPTC, esprocarb, ethalfluralin, ethametsulfuron-methyl, ethidimuron, ethiozin, ethofumesate, ethoxyfen-ethyl, ethoxy-sulfuron, etobenzanid, fenoxaprop, fenoxaprop-P, fenoxasulfone, fenquinotrione, fentrazamide, fenuron, flamprop, flamprop-M, flazasulfuron, florasulam, florpyrauxifen, fluazifop, fluazifop-P, fluazolate, flucarbazone-sodium, flucetosulfuron, fluchloralin, flufenacet, flufenpyr ethyl, flumetsulam, flumicloracpentyl, flumioxazin, flumipropin, fluometuron, fluoroglycofen, fluoronitrofen, flupoxam, flupropanate, flupyrsulfuron, flurenol, fluridone, flurochloridone, fluroxypyr, flurtamone, fluthiacet-methyl, fomesafen, foramsulfuron, fosamine, furyloxyfen, glufosinate, glufosinate-P, glyphosate, halauxifen, halosulfuron-methyl, haloxyfop, haloxyfop-P-methyl, hexazinone, imazamethabenz, imazamox, imazapic, imazapyr, imazaquin, imazethapyr, imazosulfuron, indanofan, indaziflam, iodosulfuron, iofensulfuron, ioxynil, ipfencarbazone, isopropalin, isoproturon, isouron, isoxaben, isoxachlortole, isoxaflutole, isoxapyrifop, lactofen, lancotrione, lenacil, linuron, MCPA, MCPA-thioethyl, MCPB, mecoprop, mecoprop-P, mefenacet, mesosulfuron, mesotrione, metamifop, metamitron, metazachlor, metazosulfuron, methabenzthiazuron, methazole, methiozolin, methoprotryne, methyldymron, metobenzuron, metobromuron, metolachlor, S-metolachlor, metosulam, metoxuron, metribuzin, metsulfuron, molinate, monalide, monolinuron, naproanilide, napropamide, napropamide-M, naptalam, neburon, nicosulfuron, nipyraclofen, norflurazon, orbencarb, orthosulfamuron, oryzalin, oxadiargyl, oxadiazon, oxasulfuron, oxaziclomefone, oxyfluorfen, paraquat, pebulate, pendimethalin, penoxsulam, pentanochlor, pentoxazone, pethoxamid, phenmedipham, picloram, picolinafen, piperophos, pretilachlor, primisulfuron, prodiamine, profluazol, profoxydim, proglinazine, prometon, prometryne, propachlor, propanil, propaquizafop, propazine, propham, propisochlor, propoxycarbazone, propyrisulfuron, propyzamide, prosulfocarb, prosulfuron, pyraclonil, pyraflufenethyl, pyrasulfotole, pyrazogyl, pyrazolynate, pyrazosulfuron, pyrazoxyfen, pyribenzoxim, pyributicarb, pyridafol, pyridate, pyriftalid, pyriminobac-methyl, pyrimisulfan, pyrithiobac-sodium, pyroxasulfone, pyroxsulam, quinclorac, quinmerac, quizalofop, quizalofop-P, quizalofop-P-tefuryl, rimsulfuron, saflufenacil, sethoxydim, siduron, simazine, simetryn, sulcotrione, sulfentrazone, sulfometuron-methyl, sulfosulfuron-methyl, 2,3,6-TBA, TCA-sodium, tebutam, tebuthiuron, tefuryltrione, tembotrione, tepraloxydim, terbacil, terbumeton, terbuthyl-azine, terbutryn, thenylchlor, thiazafluron, thiazopyr, thidiazimin, thiencarbazone, thifensulfuron-methyl, thiobencarb, tiafenacil, tiocarbazil, tioclorim, tolpyralate, topramezone, tralkoxydim, triafamone, triallate, triasulfuron, triaziflam, tribenuron-methyl, triclopyr, trietazine, trifloxysulfuron, trifludimoxazin, trifluralin, triflusulfuron-methyl, tritosulfuron, vernolate.

Examples of safeners that can be added to the compositions containing at least one compound having general formula (I) are the following: benoxacor, cloquintocet-mexyl, fenclorim, mefenpir-diethyl, metamphenifen.

The concentration of active substance, i.e. the concentration of the compound having general formula (I) in the above compositions can vary within a wide range, depending on the active compound, the applications for which they are intended, the environmental conditions and the type of formulation adopted. In general, the concentration of active substance preferably ranges from 1 to 90%.

Some examples are now provided, which should be considered as being descriptive and non-limitative of the present invention.

The following examples are now provided, for a better illustration of the present invention, which should be considered as being illustrative and non-limitative thereof.

EXAMPLE 1

Preparation of 1-(5-tert-butylisoxazole-3-yl)-2-cyclo-propanecarbonyloxy-3,4-dimethyl-2H-pyrrol-5-one. [Compound Nr. 4]

a) Preparation of 1-(5-tert-butylisoxazol-3-yl)-3,4-dimethylmaleimide [Intermediate Having General Formula (IV)]

A solution of 15.00 g of 3-amino-5-tert-butyl-isoxazole (107.1 mmoles)—compound having formula (IX)—and 17.60 g of 2,3-dimethylmaleic anhydride (139.2 mmoles)—compound having formula (VIII)—in 250 ml of glacial acetic acid is heated under reflux conditions for 5 hours. The system is cooled to room temperature and left under stirring for 16 hours. Upon completion of the reaction, confirmed by GC-MS control, the solvent is evaporated and the residue is dissolved in water. The aqueous solution is extracted with dichloromethane and the combined organic phases are washed with a 10% potassium carbonate solution. The organic phase is anhydrified with anhydrous sodium sulfate, filtered and concentrated. 28.09 g of the desired product are obtained, which is used without further purification in the next step. Quantitative yield

GC-MS: $M^+=248$ b) Preparation of 1-(5-tert-butylisoxazole-3-yl)-2-hydroxy-3,4-dimethyl-2H-pyrrol-5-one [Intermediate Having General Formula (II)]

A solution of 20.00 g of 1-(5-tert-butylisoxazol-3-yl)-3,4-dimethyl-maleimide (80.6 mmoles)—compound having formula (IV)—in 400 ml of anhydrous methanol is put under stirring in an inert atmosphere at room temperature for a few minutes. 1.83 g of sodium borohydride (48.4 mmoles) are carefully added to the solution in portions.

The system is left under stirring at room temperature for 16 hours. Upon completion of the reaction, confirmed by GC-MS control, the solvent is evaporated and the residue is solubilized in an aqueous solution containing 4.61 ml of glacial acetic acid (80.6 mmoles). The aqueous solution is extracted with dichloromethane and the combined organic phases are washed with water and a saturated NaCl solution. After being anhydrified with anhydrous sodium sulfate and filtered, the organic phase is concentrated obtaining 17.93 g of the desired product. Yield: 89.0%

GC-MS: $M^+=250$ c) Preparation of 1-(5-tert-butylisoxazole-3-yl)-2-cyclo-propanecarbonyloxy-3,4-dimethyl-2H-pyrrol-5-one [Compound Nr. 4]

A solution of 2.00 g of 1-(5-tert-butylisoxazole-3-yl)-2-hydroxy-3,4-dimethyl-2H-pyrrol-5-one (8.0 mmoles)— compound having formula (II)—1.67 ml of triethylamine (12.0 mmoles)—compound having formula (III)—in 65 ml of anhydrous dichloromethane is cooled with an ice bath to about 0° C. 1.09 ml of cyclopropanecarbonyl chloride (12.0 mmoles) are added dropwise to the solution. After the addition, the solution is brought to room temperature and left under stirring for 16 hours. Upon completion of the reaction, confirmed by GC-MS control, 60 ml of water are added to the solution to obtain a biphasic system. After separating the organic phase, the aqueous phase is extracted with dichloromethane. The combined organic phases are washed with a saturated NaCl solution, anhydrified with anhydrous sodium sulfate, filtered and concentrated to give 2.95 g of oil. The material thus obtained is purified by silica gel chromatography eluting with a heptane:ethyl acetate solution 9:1. 2.49 g of the desired product are obtained. Yield 98%

GC-MS: $M^+=318$
LC-MS: $MH^+=319$

EXAMPLE 2

Preparation of 1-(5-tert-butyl-1,3,4-thiadiazol-2-yl)-3,4-dimethyl-2-methoxyacetate-2H-pyrrol-5-one. [Compound Nr.2]

a) Preparation of 1-(5-tert-butyl-1,3,4-thiadiazol-2-yl)-2,3-dimethylmaleimide [Intermediate Having General Formula (IV)]

0.45 g of pyrrolidine (6.4 mmoles) and 0.38 g of glacial acetic acid (6.4 mmoles) are added to a solution of 10.00 g of 2-amino-5-tert-butyl-1,3,4-thiadiazole (63.6 mmoles)—compound having formula (IX)—and 8.02 g of 2,3-dimethylmaleic anhydride (63.6 mmoles)—compound having formula (VIII)—in 60 ml of toluene. The solution is refluxed for 2 h 30'. Upon completion of the reaction, 50 ml of a 10% aqueous solution of HCl are added to the solution, obtaining a biphasic system. After separating the organic phase, the aqueous phase is extracted with ethyl acetate. The combined organic phases are washed with a 10% solution of HCl, water and a saturated NaCl solution, anhydrified with anhydrous sodium sulfate, filtered and concentrated. The solid thus obtained is washed with cold heptane. 15.98 g of the desired product are obtained. Yield 94.8%

GC-MS: $M^+=265$ b) Preparation of 1-(5-tert-butyl-1,3,4-thiadiazol-2-yl)-3,4-dimethyl-5-hydroxy-5H-pyrrol-2-one [Intermediate Having General Formula (II)]

A solution of 15.00 g of 1-(5-tert-butyl-1,3,4-tiadiazol-2-yl)-2,3-dimethylmaleimide (56.6 mmoles)—compound having formula (IV)—in 270 ml of anhydrous methanol is stirred in an inert atmosphere at room temperature for a few minutes. 1.29 g of sodium borohydride (34.0 mmoles) are carefully added to the solution in portions. The system is left under stirring at room temperature for 16 hours. Upon completion of the reaction, confirmed by GC-MS control, the solvent is evaporated and the residue is solubilized in an aqueous solution containing 3.24 ml of glacial acetic acid (56.6 mmoles). The aqueous solution is extracted with dichloromethane and the combined organic phases are washed with water and a saturated solution of NaCl. After being anhydrified with anhydrous sodium sulfate and filtered, the organic phase is concentrated obtaining 13.22 g of the desired product. Yield: 87.4%

GC-MS: $M^+=267$ c) Preparation of 1-(5-tert-butyl-1,3,4-thiadiazol-2-yl)-3,4-dimethyl-2-methoxyacetate-2H-pyrrol-5-one [Compound Nr. 2]

0.29 ml of methoxyacetic acid (3.74 mmoles)—compound having formula (III) are added to a solution of 1.00 g of 1-(5-tert-butyl-1,3,4-thiadiazol-2-yl)-3,4-dimethyl-5-hydroxy-5H-pyrrol-2-one (3.74 mmoles)—compound having formula (II)—in 15 ml of anhydrous dichloromethane. After cooling the solution to 0° C. with an ice bath, 0.77 g of dicyclohexylcarbodiimide (3.74 mmoles) are added to the system. After the addition, the solution is brought to room temperature and left under stirring for 16 hours. Upon completion of the reaction, confirmed by GC-MS control, the solution is filtered and concentrated obtaining 2.16 g of oil. The material thus obtained is purified by chromatography on silica gel eluting with a dichloromethane:ethyl acetate solution 7:3. 1.20 g of the desired product are obtained. Yield >95%

GC-MS: $M^+=339$
LC-MS: $MH^+=340$

EXAMPLE 3

Preparation of 1-(5-tert-butyl-1,3,4-thiadiazol-2-yl)-3,4-dimethyl-2-methoxyethylcarbonate-2H-pyrrol-2-yl-5-one [Compound Nr.3]

A solution of 1.00 g of 1-(5-tert-butyl-1,3,4-thiadiazol-2-yl)-3,4-dimethyl-5-hydroxy-5H-pyrrol-2-one (3.74 mmoles)—compound having formula (II)—and 0.57 ml of triethylamine (4.12 mmoles) in 15 ml of anhydrous dichloromethane is cooled with an ice bath to about 0° C. 0.48 ml of 2-methoxyethyl chloroformate (4.12 mmoles)—compound having formula (III)—are added dropwise to the solution. After the addition, the solution is brought to room temperature and left under stirring for 16 hours. Upon completion of the reaction, confirmed by control in LC-MS, 60 ml of water are added to the solution obtaining a biphasic system. After separating the organic phase, the aqueous phase is extracted with dichloromethane. The combined organic phases are washed with a saturated NaCl solution, anhydrified with anhydrous sodium sulfate, filtered and concentrated obtaining 1.22 g of oil. The material thus obtained is purified by silica gel chromatography eluting with a heptane:ethyl acetate solution 9:1. 0.80 g of the desired product are obtained. Yield 90%

LC-MS: $MH^+=240$

EXAMPLE 4

Preparation of 1-[4-(4,4,5,5-tetramethyl-1,3,2-dioxaborolan-2-yl)-pyridin-2-yl]-2-cyclopropancarbonyloxy-3,4-dimethyl-2H-pyrrol-5-one [Compound Nr.110]

a) Preparation of 1-[4-(4,4,5,5-tetramethyl-1,3,2-dioxaborolan-2-yl)-pyridin-2-yl]-3,4-dimethylmaleimide [Intermediate Having General Formula (IV)]

A solution of 10.00 g of 2-amino-4-(4,4,5,5-tetramethyl-1,3,2-dioxaborolan-2-yl)pyridine (45.44 mmoles) and of 7.45 g of 2,3-dimethylmaleic anhydride (59.06 mmoles) in 100 ml of glacial acetic acid is refluxed for 5 h. The system is cooled at room temperature and left under stirring for 16 h. Upon completion of the reaction, confirmed by control in LC-MS, the solvent is evaporated and the residue is dissolved in water. The aqueous solution is extracted with dichloromethane and the combined organic phases are washed with a 10% potassium carbonate solution. The organic phase is washed with anhydrous sodium sulfate, filtered and concentrated. 15.00 g of the desired product are obtained, which is used in the next step as such without further purification. Quantitative yield.

GC-MS: M$^+$=328.

b) Preparation of 1-[4-(4,4,5,5-tetramethyl-1,3,2-dioxaborolan-2-yl)pyridin-2-yl]-2-hydroxy-3,4-dimethyl-2H-pyrrol-5-one [Intermediate Having General Formula (II)]

A solution of 10.00 g of 1-[4-(4,4,5,5-tetramethyl-1,3,2-dioxaborolan-2-yl)pyridin-2-yl]-3,4-dimethylmaleimide (30.50 mmoles) in 150 ml of anhydrous methanol is left under stirring under inert atmosphere at room temperature for some minutes. 0.69 g of sodium borohydride (18.3 mmoles) are added with caution to the solution. The system is left under stirring at room temperature for 4 h. Upon completion of the reaction, confirmed by control in LC-MS, the solvent is evaporated and the residue is dissolved in an aqueous solution containing 1.75 ml of glacial acetic acid (30.5 mmoles). The aqueous solution is extracted with dichloromethane and the combined organic phases are washed with water and with a saturated NaCl solution. After being anhydrified with anhydrous sodium sulfate and filtered, the organic phase is concentrated obtaining 8.05 g of the desired product. Yield: 80.0%

GC-MS: M$^+$=330 c) Preparation of 1-(4-(4,4,5,5-tetramethyl-1,3,2-dioxaborolan-2-yl)pyridin-2-yl)-2-cyclopropancarbonyloxy-3,4-dimethyl-2H-pyrrol-5-one [Compound Nr.110]

A solution of 8.00 g of 1-[4-(4,4,5,5-tetramethyl-1,3,2-dioxaborolan-2-yl)pyridin-2-yl]-2-hydroxy-3,4-dimethyl-2H-pyrrol-5-one (24.24 mmoles) and of 3.7 ml of triethylamine (26.66 mmoles) in 250 ml of anhydrous dichloromethane is cooled with an ice bath to about 0° C. 2.42 ml of cyclopropancarbonyl chloride (26.66 mmoles) are added dropwise to the solution. After the addition, the solution is brought to room temperature and left under stirring for 16 hours. Upon completion of the reaction, confirmed by control in LC-MS, 250 ml of water are added to the solution obtaining a biphasic system. After separating the organic phase, the aqueous phase is extracted with dichloromethane. The combined organic phases are washed with a saturated NaCl solution, anhydrified with anhydrous sodium sulfate, filtered and concentrated obtaining 10.2 g of oil. The material thus obtained is purified by silica gel chromatography eluting with a heptane:ethyl acetate solution 9:1. 8.8 g of the desired product are obtained. Yield 91%

GC-MS: M$^+$=398
LC-MS: MH$^+$=399

EXAMPLE 5

Preparation of Compound Nrs. 11, 14, 18, 22, 100, 101, 109, 110, 113, 114, 117-119

Operating analogously to what described in the previous examples, Compounds 11, 14, 18, 22, 100, 101, 109, 110, 113, 114, 117-119 having formula (I) indicated in Table 3, were obtained.

TABLE 3

| Comp. No | R$^1$ | R$^2$ | Z | n | R | Q | G |
|---|---|---|---|---|---|---|---|
| 11 | CH$_3$ | CH$_3$ | O | 2 | (structure) | O | (structure) |
| 14 | CH$_3$ | CH$_3$ | O | 1 | (structure) | O | (structure) |
| 18 | CH$_3$ | CH$_3$ | O | 1 | (structure) | O | (structure) |
| 22 | CH$_3$ | CH$_3$ | O | 1 | (structure) | O | (structure) |

TABLE 3-continued

| Comp. No | R¹ | R² | Z | n | R | Q | G |
|---|---|---|---|---|---|---|---|
| 100 | CH₃ | CH₃ | O | 1 | cyclopropyl C(=O)- | O | 5-tert-butyl-1,3,4-thiadiazol-2-yl |
| 101 | CH₃ | CH₃ | O | 1 | cyclopropyl C(=O)- | O | 1-methyl-5-(trifluoromethyl)-1H-pyrazol-3-yl |
| 109 | CH₃ | CH₃ | O | 1 | cyclopropyl C(=O)- | O | 4-(trifluoromethyl)pyridin-2-yl |
| 110 | CH₃ | CH₃ | O | 1 | cyclopropyl C(=O)- | O | 4-(4,4,5,5-tetramethyl-1,3,2-dioxaborolan-2-yl)pyridin-2-yl |
| 113 | CH₃ | CH₃ | O | 1 | cyclopropyl C(=O)- | O | 4-methylpyridin-2-yl |
| 114 | CH₃ | CH₃ | O | 1 | n-octyl C(=O)- | O | 5-tert-butylisoxazol-3-yl |
| 117 | CH₃ | CH₃ | O | 1 | CH₃OCH₂CH₂C(=O)- | O | 5-tert-butyl-1,3,4-thiadiazol-2-yl |
| 118 | CH₃ | CH₃ | O | 1 | CH₃OCH₂CH₂CH₂C(=O)- | O | 5-tert-butyl-1,3,4-thiadiazol-2-yl |

TABLE 3-continued

| Comp. No | R¹ | R² | Z | n | R | Q | G |
|---|---|---|---|---|---|---|---|
| 119 | CH₃ | CH₃ | O | 1 | *–C(=O)–cyclopropyl | O | *–pyrimidin-4-yl with tert-butyl substituent |

Table 4 indicates the results of the LC-MS analyses carried out on Compounds 11, 14, 18, 22, 100, 101, 109, 110, 113, 114 and 117-119.

TABLE 4

| Comp. Nr. | LC-MS: MH+ |
|---|---|
| 11 | 555 |
| 14 | 323 |
| 18 | 353 |
| 22 | 323 |
| 100 | 336 |
| 101 | 344 |
| 109 | 341 |
| 110 | 399 |
| 113 | 287 |
| 114 | 391 |
| 117 | 354 |
| 118 | 368 |
| 119 | 316 |

EXAMPLE 6

Determination of the Herbicidal Activity and Phytotoxicity in Pre-Emergence.

The herbicidal activity of the compounds of the invention in pre-emergence was evaluated according to the following operating modes.

The plant species of interest (weeds or crops) were sown in pots with a diameter of 10 cm, a height of 10 cm and containing sandy soil. Six pots of each plant species were used.

Water was added to each pot in an amount suitable for the germination of the seeds. The pots were then divided into two groups each containing 3 pots for each weed or crop.

One day after sowing, the first group of pots was treated with a dispersion having the following composition:

| | |
|---|---|
| Compound having general formula (I) | 200 mg |
| Water | 56 ml |
| Acetone | 14 ml |
| Tween 20 | 0.5% (w/w) |

The dispersion was prepared by adding a desired dose of a compound of the present invention to a hydroacetone solution containing acetone at 20% by volume and Tween 20 at 0.5% by weight, with respect to the total weight of the dispersion and applied on a surface of 2 square meters.

The weighing of each compound of the present invention corresponds to the effective dose of 1,000 g/ha.

The second group was treated only with a hydroacetone solution containing acetone at 20% by volume and Tween 20 at 0.5% by weight, and was used as a comparison term (control).

All the pots were kept under observation in a conditioned environment (greenhouse) under the following environmental conditions:
temperature: 24° C. during the day and 18° C. at night
relative humidity: >50%
photoperiod: 16 hours;
light intensity: 12,000 lux.

The pots were uniformly watered as needed, so as to ensure a degree of humidity sufficient for a good development of the plants.

Twenty-one days after treatment, the herbicidal activity was evaluated according to the percentage of damage (scale 0-100%) found on the treated plants compared to the untreated plants (control):
0%=No effect on the plants
100%=Complete death of the plants Table 5 shows the results obtained by treating the plant species indicated below with Comp. Nrs. 4 and 2 compared with a dispersion containing the Compound CR1 described in EP0297378 instead of the compound having general formula (I):
CR1=1-(5-tert-butylisoxazol-3-yl)-2-hydroxy-3,4-dimethyl-2H-pyrrol-5-one

TABLE 5

Herbicidal activity in pre-emergence at a dose of 250 g/ha

| | Compounds | | |
|---|---|---|---|
| Weeds | CR1 | Comp Nr.4 | Comp Nr.2 |
| Solanum nigra | 90 | 100 | 95 |
| Abutilon theophrasti | 90 | 100 | 95 |
| Amaranthus retroflexus | 60 | 80 | 92 |
| Lolium rigidum | 80 | 90 | 100 |
| Setaria viridis | 79 | 100 | 100 |

EXAMPLE 7

Determination of the Herbicidal Activity and Phytotoxicity in Post-Emergence

The herbicidal activity of the compounds of the invention in post-emergence was evaluated according to the following operating modes.

The plant species of interest (weeds or crops) were sown in pots with a diameter greater than 10 cm, a height of 10 cm and containing sandy soil. Six pots were used for each plant species.

Water was added to each pot in an amount suitable for the germination of the seeds. The pots were then divided into two groups each containing 3 pots for each weed or crop.

Upon reaching the phenological stage of the plants with 1-2 extended leaves (BBCH 11-12), the first group of pots was treated with the same hydroacetone dispersion containing 20% acetone by volume, the compound under evaluation at the desired dose and Tween 20 at 0.5% by weight, indicated in Example 6.

The second group was treated only with a hydroacetone solution containing acetone at 20% by volume and Tween 20 at 0.5% by weight, and was used as a comparison term (control).

All the pots were kept under observation in a conditioned environment (greenhouse) under the following environmental conditions:
temperature: 24° C. during the day and 18° C. at night
relative humidity: >50%
photoperiod: 16 hours;
light intensity: 12,000 lux.

The pots were uniformly watered as needed, so as to ensure a degree of humidity sufficient for a good development of the plants.

Twenty-one days after treatment, the herbicidal activity was evaluated according to the percentage of damage (scale 0-100%) found on the treated plants compared to the untreated plants (control):
0%=No effect on the plants
100%=Complete death of the plants Table 6 shows the results obtained by treating the plant species indicated below with Comp. Nrs. 11,4,2,3 compared with a hydroacetone dispersion containing the Compound CR1 described in EP0297378.
CR1=1-(5-tert-butylisoxazol-3-yl)-2-hydroxy-3,4-dimethyl-2H-pyrrol-5-one

TABLE 6

Herbicidal activity in post-emergence at a dose of 250 g/ha

| Weeds | Compounds | | | | |
|---|---|---|---|---|---|
|  | CR1 | Comp Nr.11 | Comp Nr.4 | Comp Nr.2 | Comp Nr.3 |
| *Sida spinosa* | 40 | 100 | 100 | 90 | 90 |
| *Echinochloa crus-galli* | 85 | 100 | 100 | 100 | 95 |
| *Digitaria sanguinalis* | 40 | 83 | 100 | 100 | 90 |

The invention claimed is:

1. A compound of general formula (I), salts, or hydrates thereof:

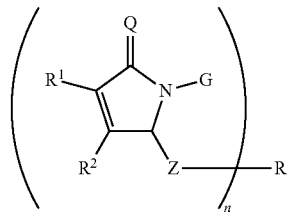

wherein:

R represents a $C_3$-$C_{18}$ cycloalkylcarbonyl group, a $C_3$-$C_{18}$ cycloalkoxycarbonyl group, a $C_3$-$C_{18}$ cycloalkyl $C_1$-$C_6$ alkylcarbonyl group, a $C_1$-$C_{12}$ alkoxy $C_1$-$C_{12}$ alkylcarbonyl group, a $C_1$-$C_{12}$ alkylcarboxy $C_1$-$C_{12}$ alkylcarbonyl group, a $C_1$-$C_{12}$ alkoxy $C_1$-$C_{12}$ alkoxycarbonyl group, an aryl $C_1$-$C_{12}$ alkoxycarbonyl group, a $C_2$-$C_6$ haloalkenylcarbonyl group, a bifunctional —(CO—CO)— group a

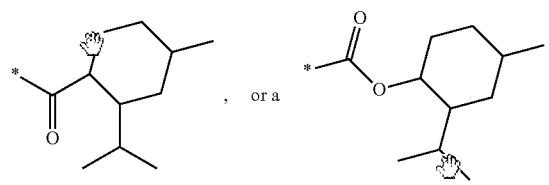 [SMILES: *C(=O)C1CCC(C)CC1C(C)C ; *C(=O)OC1CCC(C)CC1C(C)C]

, or a $R^1$ and $R^2$, equal to each other, represent a $C_1$-$C_{12}$ alkyl;
Z represents an oxygen (O) atom;
Q represents an oxygen atom;
n is 1 or 2;
G represents

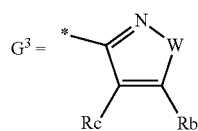

and wherein:
W represents an oxygen atom; and
Rb represents a $C_1$-$C_{12}$ alkyl and Rc represents a hydrogen atom.

2. The compound of general formula (I) of claim 1, wherein R, $R_1$, $R_2$, Z, n, Q, and G have the following meanings:

| Comp. No. | $R^1$ | $R^2$ | Z | n | R | Q | G |
|---|---|---|---|---|---|---|---|
| 4 | CH₃ | CH₃ | O | 1 | 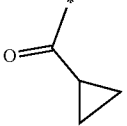 | O | 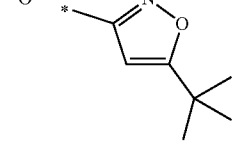 |

-continued
| Comp. No. | R¹ | R² | Z | n | R | Q | G |
|---|---|---|---|---|---|---|---|
| 5 | CH₃ | CH₃ | O | 1 | 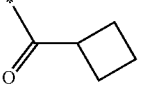 | O | 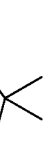 |
| 6 | CH₃ | CH₃ | O | 1 | 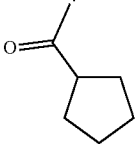 | O |  |
| 7 | CH₃ | CH₃ | O | 1 | 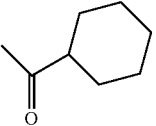 | O |  |
| 8 | CH₃ | CH₃ | O | 1 | 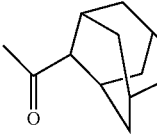 | O |  |
| 9 | CH₃ | CH₃ | O | 1 | 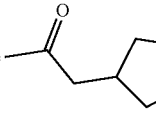 | O |  |
| 10 | CH₃ | CH₃ | O | 1 | 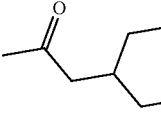 | O |  |
| 11 | CH₃ | CH₃ | O | 2 | 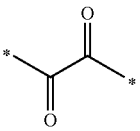 | O |  |
| 14 | CH₃ | CH₃ | O | 1 | 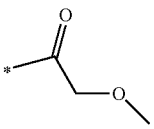 | O |  |
| 15 | CH₃ | CH₃ | O | 1 | 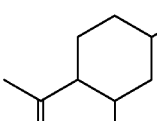 | O |  |

-continued

| Comp. No. | R¹ | R² | Z | n | R | Q | G |
|---|---|---|---|---|---|---|---|
| 17 | $CH_3$ | $CH_3$ | O | 1 | cyclopentyl ester group | O | 5-tert-butylisoxazol-3-yl |
| 18 | $CH_3$ | $CH_3$ | O | 1 | 2-methoxyethyl ester group | O | 5-tert-butylisoxazol-3-yl |
| 20 | $CH_3$ | $CH_3$ | O | 1 | menthyl ester group | O | 5-tert-butylisoxazol-3-yl |

3. The compound of general formula (I) of claim 1, wherein:
- R represents a group selected from a $C_3$-$C_{12}$ cycloalkylcarbonyl group, a $C_1$-$C_{18}$ alkoxy $C_1$-$C_{18}$ alkoxycarbonyl group, or a —(COCO)— group,
- Z represents an oxygen atom,
- Q represents an oxygen atom,
- R¹ and R², equal to each other, represent a $C_1$-$C_4$ alkyl,
- n is equal to 1 or 2, and
- G has the meaning of $G^3$ as defined in claim 1.

4. The compound of general formula (I) of claim 1, wherein:
- R represents a group selected from a cyclopropylcarbonyl group, a methoxymethylcarbonyl group, a methoxyethoxycarbonyl group, or a —(COCO)— group,
- R¹ and R² are methyl or ethyl,
- Z represents an oxygen atom,
- Q represents an oxygen atom,
- n is equal to 1 or 2, and
- G has the meaning of $G^3$ as defined in claim 1.

5. The compound of general formula (I) of claim 1, wherein: R, R¹, R², Z, Q, G, and n have the following meanings:

| Comp. No. | R¹ | R² | Z | n | R | Q | G |
|---|---|---|---|---|---|---|---|
| 4 | $CH_3$ | $CH_3$ | O | 1 | cyclopropylcarbonyl | O | 5-tert-butylisoxazol-3-yl |
| 11 | $CH_3$ | $CH_3$ | O | 2 | —(COCO)— | O | 5-tert-butylisoxazol-3-yl |
| 14 | $CH_3$ | $CH_3$ | O | 1 | methoxymethylcarbonyl | O | 5-tert-butylisoxazol-3-yl |

-continued

| Comp. No. | R¹ | R² | Z | n | R | Q | G |
|---|---|---|---|---|---|---|---|
| 18 | $CH_3$ | $CH_3$ | O | 1 | 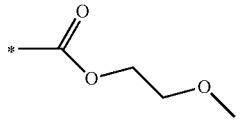 | O | 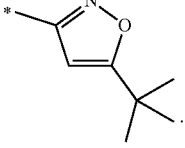 |

6. A herbicide composition, comprising:
  at least one compound of general formula (I) of claim 1;
  at least one solvent and/or at least one diluent; and
  optionally, at least one agronomically acceptable excipient.

7. The herbicide composition of claim 6, further comprising at least one additional active ingredient, compatible with the at least one compound of general formula (I), selected from:
  herbicides different from those of general formula (I), fungicides, insecticides, acaricides, fertilisers, phytoprotectors, and mixtures thereof.

8. The herbicide composition of claim 6, wherein the compound of general formula (I) is present in a concentration within a range of 1%-90% by weight relative to a total weight of the herbicide composition.

9. A method for controlling at least one weed in an agricultural crop, the method comprising:
  applying the compound of general formula (I) of claim 1 as a herbicide.

10. A method for controlling at least one weed in an agricultural crop, the method comprising:
  applying the herbicide composition of claim 6 as a herbicide.

11. A method for controlling at least one weed in pre-emergence or post-emergence in an agricultural crop, the method comprising: applying the compound of general formula (I) of claim 1 as a herbicide.

12. A method for controlling at least one weed in pre-emergence or post-emergence in an agricultural crop, the method comprising: applying the herbicide composition of claim 6 as a herbicide.

13. The method of claim 9, where the at least one weed is selected from: *Abutilon* theofrasti, *Alisma plantago*, *Amaranthus* spp., *Amni maius*, *Capsella* bursa *pastoris*, *Chenopodium album*, *Convolvulus sepium*, *Galium aparine*, *Geranium dissectum*, *Heteranthera* spp., *Ipomea* spp., *Matricaria* spp., *Papaver* rhoaes, *Phaseolus aureus*, *Polygonum persicaria*, *Portulaca oleracea*, *Setaria viridis*, *Sida spinosa*, *Sinapsis arvensis*, *Solanum nigrum*, *Stellaria media*, Veronica spp., *Viola* spp., *Xanthium* spp., *Alopecurus myosuroides*, Anisanta spp., *Apera spica-venti*, *Avena* spp., *Cyperus* spp., *Digitaria sanguinalis*, *Eleusine* spp., *Echinochloa* spp., *Eleocharis* avicularis, *Lolium* spp., *Panicum* spp., *Poa* spp., *Scirpus* spp., or *Sorghum* spp.

14. The method of claim 10, where the at least one weed is selected from: *Abutilon* theofrasti, *Alisma plantago*, *Amaranthus* spp., *Amni maius*, *Capsella* bursa *pastoris*, *Chenopodium album*, *Convolvulus sepium*, *Galium aparine*, *Geranium dissectum*, *Heteranthera* spp., *Ipomea* spp., *Matricaria* spp., *Papaver* rhoaes, *Phaseolus aureus*, *Polygonum persicaria*, *Portulaca oleracea*, *Setaria viridis*, *Sida spinosa*, *Sinapsis arvensis*, *Solanum nigrum*, *Stellaria media*, Veronica spp., *Viola* spp., *Xanthium* spp., *Alopecurus myosuroides*, Anisanta spp., *Apera spica-venti*, *Avena* spp., *Cyperus* spp., *Digitaria sanguinalis*, *Eleusine* spp., *Echinochloa* spp., *Eleocharis* avicularis, *Lolium* spp., *Panicum* spp., *Poa* spp., *Scirpus* spp., or *Sorghum* spp.

15. The method of claim 9, where the agricultural crop is selected from: wheat (*Triticum* sp.), barley (*Hordeum vulgare*), maize (*Zea mays*), and soy (*Glycine max*).

16. The method of claim 10, where the agricultural crop is selected from: wheat (*Triticum* sp.), barley (*Hordeum vulgare*), maize (*Zea mays*), and soy (*Glycine max*).

17. A method for controlling at least one weed in an agricultural crop, the method comprising:
  applying at least one effective dose of at least one compound of general formula (I) of claim 1 to the agricultural crop.

18. A method for controlling at least one weed in an agricultural crop, the method comprising:
  applying at least one effective dose of at least one herbicide composition of claim 6 to the agricultural crop.

19. A process for preparing the compound of general formula (I) of claim 1, the process comprising:
  reacting a compound of general formula (II) with at least one compound of general formula (III) in a presence of at least one base, according to:

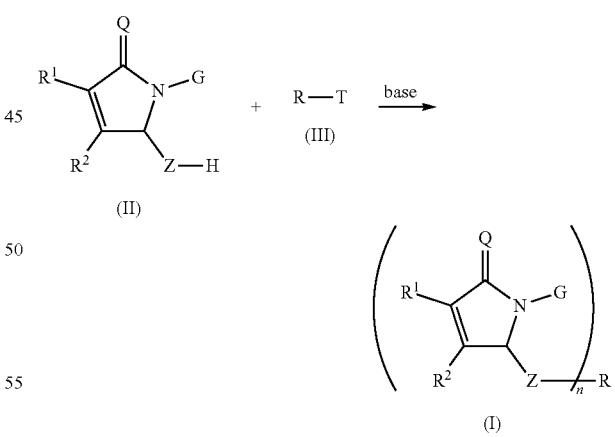

wherein R, R¹, R², Z, Q, n, and G have meanings as defined in claim 1, and wherein T represents a leaving group.

20. A process for preparing the compound of general formula (I) of claim 1, the process comprising:
  reacting a compound of general formula (VI) with at least one compound of general formula (VII) in a presence of at least one base, according to:

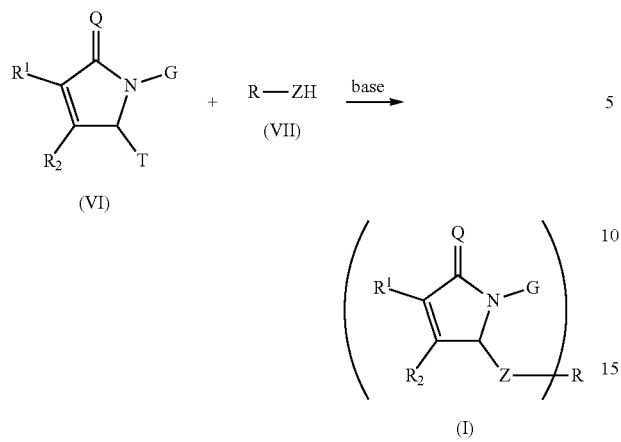
wherein R, $R^1$, $R^2$, Z, Q, n, and G have meanings as defined in claim 1, and wherein T represents a leaving group.
* * * * *